United States Patent
Wang et al.

(10) Patent No.: US 11,352,368 B2
(45) Date of Patent: Jun. 7, 2022

(54) SALT OF FUSED RING PYRIMIDINE COMPOUND, CRYSTAL FORM THEREOF AND PREPARATION METHOD THEREFOR AND USE THEREOF

(71) Applicant: GUANGZHOU MAXINOVEL PHARMACEUTICALS CO., LTD., Guangdong (CN)

(72) Inventors: Yuguang Wang, Shanghai (CN); Nong Zhang, Shanghai (CN); Pingjing Zhang, Shanghai (CN)

(73) Assignee: GUANGZHOU MAXINOVEL PHARMACEUTICALS CO., LTD., Guangdong (CN)

( * ) Notice: Subject to any disclaimer, the term of this patent is extended or adjusted under 35 U.S.C. 154(b) by 0 days.

(21) Appl. No.: 17/058,151

(22) PCT Filed: May 10, 2019

(86) PCT No.: PCT/CN2019/086373
§ 371 (c)(1),
(2) Date: Nov. 24, 2020

(87) PCT Pub. No.: WO2019/228171
PCT Pub. Date: Dec. 5, 2019

(65) Prior Publication Data
US 2021/0198275 A1    Jul. 1, 2021

(30) Foreign Application Priority Data
May 31, 2018   (CN) .......................... 201810551904.1

(51) Int. Cl.
| C07D 495/04 | (2006.01) |
| A61K 31/519 | (2006.01) |
| A61P 35/00 | (2006.01) |
| A61P 35/02 | (2006.01) |
| C07C 57/15 | (2006.01) |

(52) U.S. Cl.
CPC ........ *C07D 495/04* (2013.01); *C07B 2200/13* (2013.01)

(58) Field of Classification Search
CPC .............. C07D 495/04; C07B 2200/13; A61K 31/519; A61P 35/00; A61P 35/02; C07C 57/15
See application file for complete search history.

(56) References Cited

U.S. PATENT DOCUMENTS

| 10,494,378 B2* | 12/2019 | Xu ...................... A61K 31/519 |
| 2013/0261106 A1 | 10/2013 | Carry et al. |
| 2018/0127420 A1 | 5/2018 | Zhang et al. |
| 2018/0208604 A1 | 7/2018 | Xu et al. |

FOREIGN PATENT DOCUMENTS

| AU | 2016295594 A1 | 3/2018 |
| CN | 106220644 A | 12/2016 |
| CN | 106279201 A | 1/2017 |
| CN | 106366093 A | 2/2017 |
| CN | 107652303 A | 2/2018 |

OTHER PUBLICATIONS

Donnez, J., "Uterine fibroid management: from the present to the future." Human reproduction update 22.6 (2016): 665-686.*
Skin Cancer Prevention—The Skin Cancer Foundation, 2015 p. 1-3; https://www.skincancer.org/skin-cancer-prevention.*
Verweij, M., 2000 Preventive Medicine Between Obligation and Aspiration 2000, Springer Science and Business Media p. 1-190; Ch. 3; 31 p.*
Serajuddin, A.T.M. "Salt formation to improve drug solubility." Advanced drug delivery reviews 59.7 (2007): 603-616.*
Aug. 20, 2019 International Search Report issued in International Patent Application No. PCT/CN2019/086373.
Aug. 20, 2019 Written Opinion of the International Searching Authority issued in International Patent Application No. PCT/CN2019/086373.

(Continued)

*Primary Examiner* — John M Mauro
(74) *Attorney, Agent, or Firm* — Houston Beshining Law Office PLLC; Liangang Ye

(57) ABSTRACT

Disclosed are a salt of a fused ring pyrimidine compound, a crystal form thereof and a preparation method therefor and the use thereof. The fused ring pyrimidine compound is N-[7-(4-fluoro-2-methoxyphenyl)-6-methylthieno[3,2-d]pyrimidin-2-yl]-1-(piperidin-4-yl)-1H-pyrazol-4-amine, having a structure as shown in formula 1. The preparation methods in the invention for the salt of the fused ring pyrimidine compound and the crystal form thereof are simple; and the salt of the fused ring pyrimidine compound and the crystal form thereof at least have the characteristics of having a better stability, not easily absorbing moisture, being of a polycrystalline type, having a chemical stability and pharmacokinetics, and having an improved solubility.

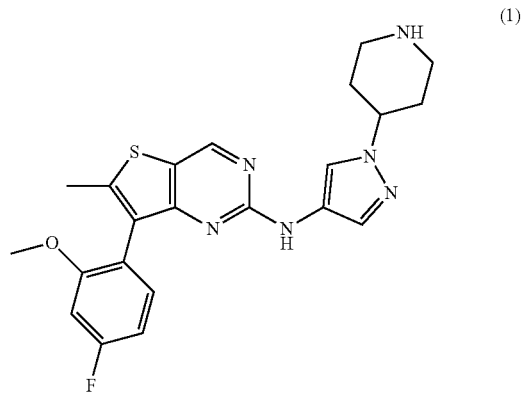

(1)

16 Claims, 5 Drawing Sheets

(56) References Cited

OTHER PUBLICATIONS

Aaronson, D.S. et al. Science 2002, 296, 1653-1655.
O' Shea, J.J. et al. Nat. Rev. Drug Discovery 2004, 3, 555-564.
Kiesseleva T. et al. J. Gene, 2002, 285, 1-24.
J. Folkman. Nat. Med. 1995, 1, 27-31.
Dec. 7, 2021 the PESR issued in European application No. 19810593.4.
Oct. 21, 2021 The First Office Action issued in Chinese patent application No. 2019103714523.
Extended European Search Report dated Mar. 22, 2022 issued in European Patent Application No. 19810593.4.

\* cited by examiner

SALT OF FUSED RING PYRIMIDINE COMPOUND, CRYSTAL FORM THEREOF AND PREPARATION METHOD THEREFOR AND USE THEREOF

The present application is a National Stage of International Application No. PCT/CN2019/086373, filed on May 10, 2019, which claims the priority of Chinese patent application CN 201810551904.1 filed on May 31, 2018. The aforementioned Chinese patent application is incorporated into the present application by reference in its entirety.

TECHNICAL FIELD

Disclosed are a salt of fused ring pyrimidine compound, a crystal form thereof and a preparation method therefor and the use thereof.

BACKGROUND

JAK-STAT (Janus kinase—signal transducer and activator of transcription) signaling pathway is a signal transduction pathway stimulated by cytokine and participates in many important biological processes such as cell proliferation, differentiation, apoptosis and immune regulation (Aaronson, D. S. et al. Science 2002, 296, 1653-1655; O'Shea, J. J. et al. *Nat. Rev. Drug Discovery* 2004, 3, 555-564). JAK-STAT signaling pathway is widely exist in various tissues and cells in the body, especially plays an important role in the differentiation, proliferation and anti-infection of lymphoid cell lines, and participates in the interaction and signal transduction of various inflammatory factors (Kiesseleva T. et al. *J. Gene,* 2002, 285, 1-24). Genesis, growth, invasion and metastasis of tumors are related to JAK-STAT signal transduction pathway. Fibroblast growth factor receptor family belongs to a new receptor kinase family, which includes four receptor subtypes (FGFR-1, 2, 3 and 4) encoding by four closely related genes, and some isomeric molecules. FGFR can promote the migration, proliferation and differentiation of endothelial cells, and plays an important role in the regulation of vascularization and angiogenesis. Uncontrolled angiogenesis will lead to the genesis of tumors and the growth of metastatic tumors (J. Folkman. *Nat. Med.* 1995, 1, 27-31.). Fms-like tyrosine kinase 3 (FLT3) belongs to receptor tyrosine kinase III (RTK III) family member, is mainly expressed in the precursor of normal myeloid cells, but its abnormal expression is also found in a very large portion of acute myeloid leukemia (AML) cells. Src family kinase (SFK) is a class of non-receptor tyrosine kinase family. Their abnormal activation and expression lead to the occurrence and development of a wide range of diseases, such as a large number of solid tumors, various hematological malignancies and some neuronal pathology.

Patent CN 106366093 A discloses a fused ring pyrimidine compound with a chemical structural formula of

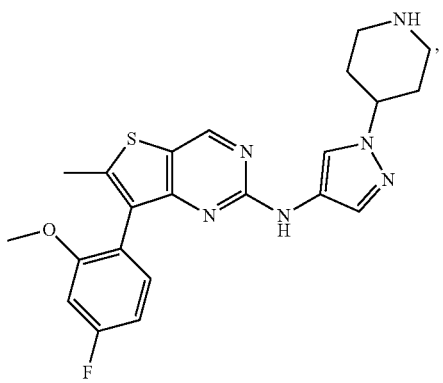

which has a good inhibitory effect on JAK, FGFR, FLT3 and Src kinase.

In addition to a good inhibitory activity on kinases, as a candidate drug for the treatment of tumors, the salt form and crystal form of the fused ring pyrimidine compound have a crucial impact on the stability of drugs during production, processing, storage and transportation, and the bioavailability of drugs during the treatment. Moreover, the chemical stability, solid state stability and shelf life of active ingredients are very important factors from the perspective of obtaining a commercially viable production method or from the perspective of producing pharmaceutical compositions containing active compounds. Therefore, it is very important to provide an appropriate form of a drug with required properties for drug production and storage.

CONTENT OF THE PRESENT INVENTION

The technical problem to be solved by the present disclosure is to overcome the defects of low solubility, easily absorbing moisture, low absorption rate, low stability and low dissolution rate of the fused ring pyrimidine compound in the prior art in the process of drug preparation, so as to provide a salt of fused ring pyrimidine compound shown in formula 1, a crystal form thereof and a preparation method therefor and the use thereof. The preparation methods in the present disclosure for the salt of the fused ring pyrimidine compound and the crystal form thereof are simple; and the salt of the fused ring pyrimidine compound and the crystal form thereof at least have the characteristics of having a better solubility and stability, not easily absorbing moisture, good pharmacokinetics, easy for drugs to disperse, prepare and use, and having an important value for the optimization and development of drugs.

The present disclosure provides a salt of the fused ring pyrimidine compound as shown in formula 1, and the salt is fumarate, adipate, phosphate or tartrate of the fused ring pyrimidine compound as shown in formula 1,

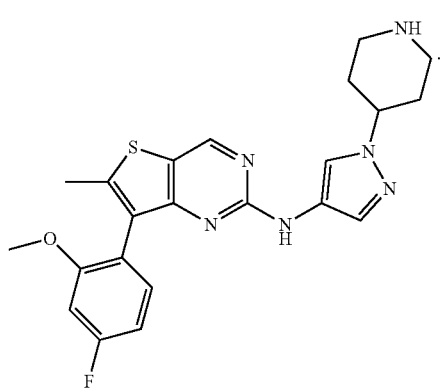 [SMILES: COc1cc(F)ccc1-c1c(C)sc2cnc(Nc3cnn(C4CCNCC4)c3)nc12 ; ","]

The fumarate of the fused ring pyrimidine compound as shown in formula 1 is a compound formed by the fused ring pyrimidine compound as shown in formula 1 and fumaric acid in a molar ratio of 1:0.5, and the structural formula thereof is as shown in formula 2:

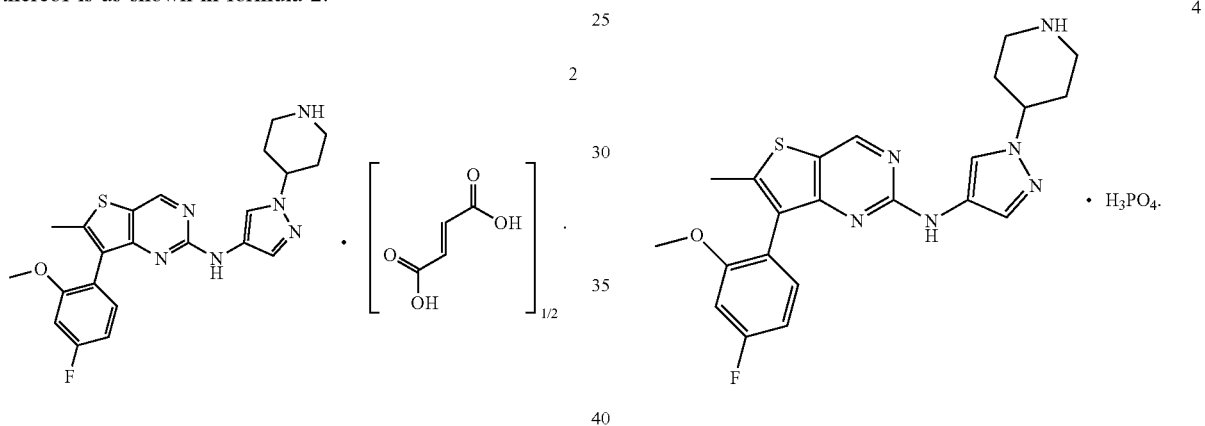

The adipate of the fused ring pyrimidine compound as shown in formula 1 is a compound formed by the fused ring pyrimidine compound as shown in formula 1 and adipic acid in a molar ratio of 1:0.5, and the structural formula thereof is as shown in formula 3:

The phosphate of the fused ring pyrimidine compound as shown in formula 1 is a compound formed by the fused ring pyrimidine compound as shown in formula 1 and phosphoric acid in a molar ratio of 1:1, and the structural formula thereof is as shown in formula 4:

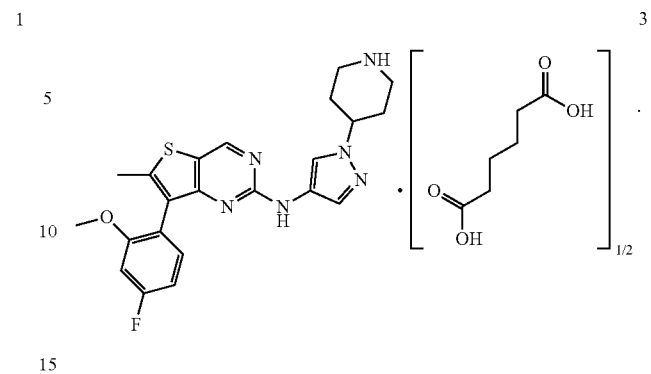

The tartrate of the fused ring pyrimidine compound as shown in formula 1 is a compound formed by the fused ring pyrimidine compound as shown in formula 1 and tartaric acid in a molar ratio of 1:0.5, and the structural formula thereof is as shown in formula 5:

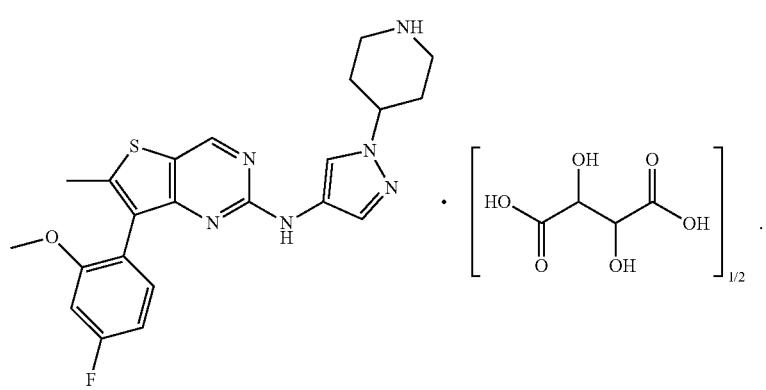

The salt of the fused ring pyrimidine compound as shown in formula 1, preferably the fumarate of the fused ring pyrimidine compound, as shown in formula 2 or the adipate of the fused ring pyrimidine compound, as shown in formula 3; more preferably, the fumarate of the fused ring pyrimidine compound, as shown in formula 2.

The tartrate of the fused ring pyrimidine compound as shown in formula 1 can also comprise water molecules.

The present disclosure further provides a crystal form A of the fumarate of fused ring pyrimidine compound as shown in formula 2, the X-ray powder diffraction pattern (XRPD) of the crystal form A represented by diffraction angle 2θ (2θ±0.2° values has characteristic peaks at 7.311°, 8.161°, 9.397°, 12.341, 14.679°, 15.331°, 15.755°, 17.255°, 18.664°, 19.207°, 19.707°, 21.207°, 21.701° and 23.423°,

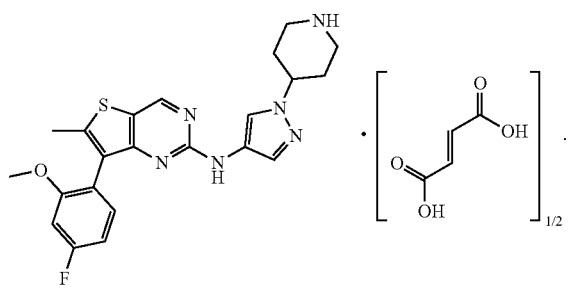

2

The X-ray diffraction characteristic peak and relative intensity in the X-ray powder diffraction pattern of the crystal form A of the fumarate of fused ring pyrimidine compound as shown in formula 2 is as shown in table 1;

TABLE 1

| No. | 2θ(2θ ± 0.2°) | Relative intensity % |
|---|---|---|
| 1 | 7.311 | 27.6 |
| 2 | 8.161 | 3.7 |
| 3 | 9.397 | 3.7 |
| 4 | 12.341 | 4.8 |
| 5 | 14.679 | 100 |
| 6 | 15.331 | 5.1 |
| 7 | 15.755 | 17.4 |
| 8 | 17.255 | 2.8 |
| 9 | 18.664 | 11.2 |
| 10 | 19.207 | 6.1 |
| 11 | 19.707 | 2.9 |
| 12 | 21.207 | 4.3 |
| 13 | 21.701 | 4.5 |
| 14 | 23.423 | 11 |

The X-ray powder diffraction pattern of the crystal form A of the fumarate of fused ring pyrimidine compound as shown in formula 2 can also be substantially as shown in FIG. 2.

The X-ray powder diffraction is measured using Kα spectral line of Cu target.

The characteristic absorption peak and intensity in infrared absorption spectrum (IR) diagram of the crystal form A of the fumarate of fused ring pyrimidine compound as shown in formula 2 are as shown in table 2;

TABLE 2

| No. | Absorption peak wave number (cm$^{-1}$) | Intensity % |
|---|---|---|
| 1 | 3284 | 95.15 |
| 2 | 3005 | 96.93 |
| 3 | 2962 | 89.56 |
| 4 | 2933 | 93.43 |
| 5 | 1624 | 73.28 |
| 6 | 1606 | 57.47 |
| 7 | 1595 | 47.01 |
| 8 | 1560 | 27.7 |
| 9 | 1492 | 62.77 |
| 10 | 1408 | 32.96 |
| 11 | 1352 | 39.55 |
| 12 | 663 | 62.49 |

In the thermogravimetic analysis (TGA) of the crystal form A of the fumarate of fused ring pyrimidine compound as shown in formula 2, 0.1353% weight loss occurs from 31.05° C. to 119.97° C., which is a trace amount of free water or solvent on the surface; and 4.161% weight loss occurs from 119.97° C. to 260.83° C. The percentage is weight percentage.

The thermogravimetric analysis diagram of the crystal form A of the fumarate of fused ring pyrimidine compound as shown in formula 2 can also be substantially as shown in FIG. 3.

In the dynamic vapor sorption (DVS) diagram of the crystal form A of the fumarate of fused ring pyrimidine compound as shown in formula 2, the weight gain can be 0.2518% in the range of 0% to 95% relative humidity. The percentage is weight percentage.

The dynamic vapor sorption diagram of the crystal form A of the fumarate of fused ring pyrimidine compound as shown in formula 2 can also be substantially as shown in FIG. 4.

In the differential scanning calorimetry (DSC) diagram of the crystal form A of the fumarate of fused ring pyrimidine compound as shown in formula 2, an absorption peak occurs at 262° C.±5° C., and the melting heat can be 162.6 J/g.

The differential scanning calorimetry diagram of the crystal form A of the fumarate of fused ring pyrimidine compound as shown in formula 2 can also be substantially as shown in FIG. 5.

The crystal form A of the fumarate of fused ring pyrimidine compound as shown in formula 2 is generally an anhydride.

The present disclosure further provides a crystal form B of the adipate of fused ring pyrimidine compound as shown in formula 3, the X-ray powder diffraction pattern of the crystal form B represented by diffraction angle 2θ (2θ±0.2°) values has characteristic peaks at 5.717°, 6.637°, 11.422°, 13.271°, 15.456°, 16.528°, 19.971°, 20.936°, 23.002° and 26.959°;

3

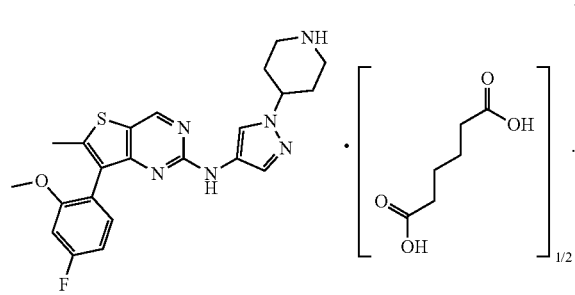

The X-ray diffraction characteristic peak and relative intensity in the X-ray powder diffraction pattern of the crystal form B of the adipate of fused ring pyrimidine compound as shown in formula 3 is as shown in table 3;

TABLE 3

| No. | 2θ(2θ ± 0.2°) | Relative intensity % |
|-----|---------------|----------------------|
| 1   | 5.717         | 8.9                  |
| 2   | 6.637         | 23.8                 |
| 3   | 11.422        | 11.7                 |
| 4   | 13.271        | 3.9                  |
| 5   | 15.456        | 21.5                 |
| 6   | 16.528        | 100                  |
| 7   | 19.971        | 3.5                  |
| 8   | 20.936        | 8.9                  |
| 9   | 23.002        | 18.2                 |
| 10  | 26.959        | 17.2                 |

The X-ray powder diffraction pattern of the crystal form B of the adipate of fused ring pyrimidine compound as shown in formula 3 can also be substantially as shown in FIG. 7.

In the present disclosure, the X-ray powder diffractions are all measured using Kα spectral line of Cu target.

In the thermogravimetic analysis of the crystal form B of the adipate of fused ring pyrimidine compound as shown in formula 3, 0.6249% weight loss occurs from 18.2° C. to 120° C., which is a trace amount of free water or solvent on the surface; and 1.567% weight loss occurs from 120° C. to 228° C. The percentage is weight percentage.

The thermogravimetric analysis diagram of the crystal form B of the adipate of fused ring pyrimidine compound as shown in formula 3 can also be substantially as shown in FIG. 8.

In the dynamic vapor sorption (DVS) of the crystal form B of the adipate of fused ring pyrimidine compound as shown in formula 3, the weight gain can be 2.751% in the relative humidity range of 0% to 95%. The percentage is weight percentage.

The dynamic vapor sorption diagram of the crystal form B of the adipate of fused ring pyrimidine compound as shown in formula 3 can also be substantially as shown in FIG. 9.

In the differential scanning calorimetry (DSC) of the crystal form B of the adipate of fused ring pyrimidine compound as shown in formula 3, an absorption peak range occurs at 229° C.±5° C., and the melting heat can be 144.1 J/g.

The differential scanning calorimetry of the crystal form B of the adipate of fused ring pyrimidine compound as shown in formula 3 can also be substantially as shown in FIG. 10.

The crystal form B of the adipate of fused ring pyrimidine compound as shown in formula 3 is generally an anhydride.

Those skilled in the art know that the peak intensity and/or peaks situation of X-ray powder diffraction may vary due to different experimental conditions. At the same time, the measured 2θ value will have an error of about ±0.2 degrees due to different accuracy of the instrument. The relative intensity value of the peak is more depend on some properties of the tested sample, such as the size and purity of the crystal, than the peak position. Therefore, the deviation of the peak intensity measured may be about ±20%. Although the existence of experimental errors, instrument errors and preferential orientation, etc., those skilled in the art can also obtain sufficient information for identifying crystal forms from the X-ray powder diffraction data provided in this patent. In DSC measurement, the initial temperature and maximum temperature data obtained by actual measurement are variable to a certain extent according to the heating rate, crystal shape and purity and other measurement parameters.

The present disclosure further provides a method for preparing the salt of the fused ring pyrimidine compound as shown in formula 1, which comprises the following steps: reacting the fused ring pyrimidine compound as shown in formula 1 with an acid in a solvent, wherein the acid is one of fumaric acid, adipic acid, phosphoric acid and tartaric acid;

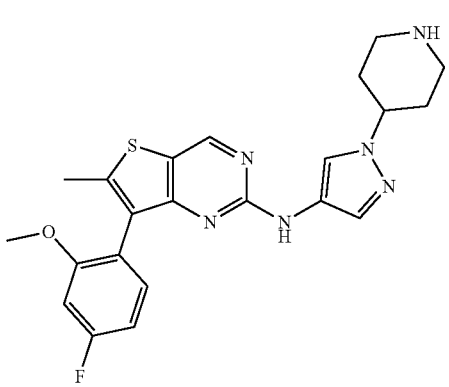

The fumarate of the fused ring pyrimidine compound as shown in formula 1 is obtained by reacting the fused ring pyrimidine compound as shown in formula 1 with fumaric acid; the adipate of the fused ring pyrimidine compound as shown in formula 1 is obtained by reacting the fused ring pyrimidine compound as shown in formula 1 with adipic acid; the phosphate of the fused ring pyrimidine compound as shown in formula 1 is obtained by reacting the fused ring pyrimidine compound as shown in formula 1 with phosphoric acid; and the tartrate of the fused ring pyrimidine compound as shown in formula 1 is obtained by reacting the fused ring pyrimidine compound as shown in formula 1 with tartaric acid.

The preparation method of the salt of the fused ring pyrimidine compound can be a conventional preparation method for such a reaction in the art.

The solvent is generally a mixed solvent, preferably one of the mixed solvent of ketones and water, the mixed solvent of alcohols and water, and the mixed solvent of ethers and water; more preferably, one of the mixed solvent of acetone and water, the mixed solvent of methanol or ethanol and water, and the mixed solvent of tetrahydrofuran and water; most preferably, one of a mixed solvent of acetone with 78% to 88% mass percentage concentration and water, a mixed solvent of methanol or ethanol with 90% mass percentage concentration and water, and a mixed solvent of tetrahydrofuran with 88% mass percentage concentration and water; and for example, the mixed solvent of acetone with 88% mass percentage concentration and water.

The mass percentage concentration is a mass fraction, which is expressed by concentration expressed as a mass percentage of the solute in the total solution.

The molar ratio of the acid to the fused ring pyrimidine compound as shown in formula 1 can be 0.5:1 to 3:1, such as 1.2:1.

The volume-to-mass ratio of the volume of the solvent to the mass of the fused ring pyrimidine compound as shown in formula 1 can be 40 mL/g to 120 mL/g, preferably 50 mL/g to 110 mL/g, such as 100 mL/g.

The reaction temperature can be a conventional temperature of such reaction in the art, preferably 20° C. to 70° C., more preferably 45° C. to 55° C., such as 50° C.

Wherein, the reaction time can be the time that the fused ring pyrimidine compound as shown in formula 1 is no longer react or the fused ring pyrimidine compound is completely consumed by detection (such as TLC), preferably 1-20 hours, such as 1 hour.

The method for preparing the salt of the fused ring pyrimidine compound comprises preferably dropwise adding the solution of the acid into "the mixture of the fused ring pyrimidine compound as shown in formula 1 and the solvent" for reacting.

The molar concentration of the solution of the acid can be 0.100 mol/L to 0.500 mol/L, such as 0.250 mol/L.

The mixing method of the fused ring pyrimidine compound as shown in formula 1 and the solvent is preferably to add the fused ring pyrimidine compound as shown in formula 1 into the solvent, so as to obtain "the mixture of the fused ring pyrimidine compound as shown in formula 1 and the solvent".

The method for preparing the salt of the fused ring pyrimidine compound can further comprise the following processing steps after the reaction is completed: cooling the reaction to room temperature followed by filtration. The cooling rate is preferably 5° C./h. After the filtration, the operation of washing the filter cake with the mixed solvent can be further comprised. After washing the filter cake, the operation of drying the filter cake can be further comprised; the drying is preferably vacuum drying; and the vacuum drying time is preferably 12 to 16 hours.

The present disclosure further provides a method for preparing the crystal form A of the fumarate of fused ring pyrimidine compound as shown in formula 2, which comprises the following steps: reacting an alcoholic solution of fumaric acid with a mixture of the fused ring pyrimidine compound as shown in formula 1 and a mixed solvent; wherein the mixed solvent is one of a mixed solvent of ketones and water, a mixed solvent of alcohols and water, and a mixed solvent of ethers and water;

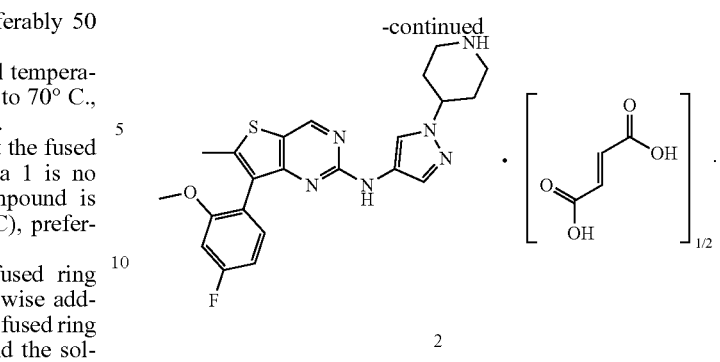

The reaction preferably involves dropwise adding the alcoholic solution of fumaric acid into the solution of the fused ring pyrimidine compound as shown in formula 1 and the mixed solvent for reaction.

The mixing method of the fused ring pyrimidine compound as shown in formula 1 and the mixed solvent is preferably to add the fused ring pyrimidine compound as shown in formula 1 into the mixed solvent, so as to obtain "the mixture of the fused ring pyrimidine compound as shown in formula 1 and the mixed solvent".

The alcoholic solution of fumaric acid is preferably methanol solution of fumaric acid or ethanol solution of fumaric acid.

The mixed solvent can be one of the mixed solvent of acetone and water, the mixed solvent of methanol or ethanol and water, and the mixed solvent of tetrahydrofuran and water; preferably, one of a mixed solvent of acetone with 78% to 88% mass percentage concentration and water, a mixed solvent of methanol or ethanol with 90% mass percentage concentration and water, and a mixed solvent of tetrahydrofuran with 88% mass percentage concentration and water; more preferably, the mixed solvent of acetone with 88% mass percentage concentration and water.

The mass percentage concentration is a mass fraction, which is expressed by concentration expressed as a mass percentage of the solute in the total solution.

The molar concentration of the alcoholic solution of fumaric acid can be 0.100 mol/L to 0.500 mol/L, preferably 0.125 mol/L to 0.250 mol/L, more preferably 0.125 mol/L.

The volume-to-mass ratio of the volume of the mixed solvent to the mass of the fused ring pyrimidine compound as shown in formula 1 can be 40 mL/g to 110 mL/g, preferably 50 mL/g to 100 mL/g, such as 50 mL/g.

The molar ratio of the fumaric acid to the fused ring pyrimidine compound as shown in formula 1 can be a conventional molar ratio in the art, preferably 0.5:1 to 3:1, more preferably 0.55:1 to 1.1:1, and most preferably 0.55:1.

The temperature of the reaction can be 20° C. to 60° C., preferably 45° C. to 55° C., and more preferably 50° C.

The reaction time can be the time that the above-mentioned fused ring pyrimidine compound as shown in formula 1 is no longer react or the above-mentioned fused ring pyrimidine compound as shown in formula 1 is completely consumed by detection (such as TLC), preferably 1-26 hours, such as 20 hour.

In the preparation method of the crystal form A of the fumarate of fused ring pyrimidine compound as shown in formula 2, after the reaction is completed, the following processing steps can be further comprised: cooling the reaction solution to room temperature followed by filtration. The cooling rate is preferably 5° C./h. After the filtration, the operation of washing a resulting filter cake with the mixed solvent can be further comprised. After washing the filter cake, the operation of drying the filter cake can be further comprised; the drying is preferably vacuum drying; and the drying time is preferably 10 hours.

The present disclosure further provides a method for preparing the crystal form B of the adipate of fused ring pyrimidine compound as shown in formula 3, which comprises the following steps: reacting an alcoholic solution of adipic acid with a mixture of the fused ring pyrimidine compound as shown in formula 1 and a mixed solvent; wherein the mixed solvent is one of a mixed solvent of ketones and water, a mixed solvent of alcohols and water, and a mixed solvent of ethers and water;

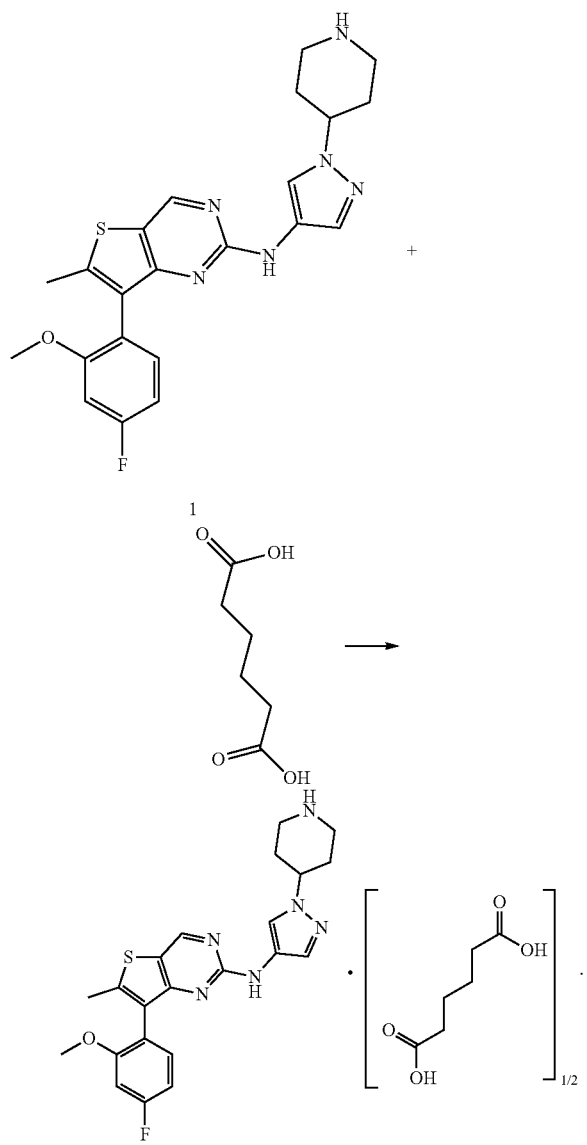

The reaction preferably involves dropwise adding the alcoholic solution of adipic acid into the solution of the fused ring pyrimidine compound as shown in formula 1 and a mixed solvent for reaction.

The mixing method of the fused ring pyrimidine compound as shown in formula 1 and the mixed solvent is preferably to add the fused ring pyrimidine compound as shown in formula 1 into the mixed solvent, so as to obtain "the mixture of the fused ring pyrimidine compound as shown in formula 1 and the mixed solvent".

The alcoholic solution of adipic acid is preferably a methanol solution of adipic acid or an ethanol solution of adipic acid.

The mixed solvent can be one of the mixed solvent of acetone and water, the mixed solvent of methanol or ethanol and water, and the mixed solvent of tetrahydrofuran and water; preferably, one of a mixed solvent of acetone with 78% to 88% mass percentage concentration and water, a mixed solvent of methanol or ethanol with 90% mass percentage concentration and water, and a mixed solvent of tetrahydrofuran with 88% mass percentage concentration and water; more preferably, the mixed solvent of acetone with 88% mass percentage concentration and water.

The mass percentage concentration is a mass fraction, which is expressed by concentration expressed as a mass percentage of the solute in the total solution.

The molar concentration of the alcoholic solution of adipic acid can be 0.100 mol/L to 0.500 mol/L, preferably 0.125 mol/L to 0.250 mol/L, such as 0.250 mol/L.

The volume-to-mass ratio of the volume of the mixed solvent to the mass of the fused ring pyrimidine compound as shown in formula 1 can be 40 mL/g to 110 mL/g, preferably 50 mL/g to 100 mL/g, such as 100 mL/g.

The molar ratio of the adipic acid to the fused ring pyrimidine compound as shown in formula 1 can be 0.5:1 to 3:1, preferably 0.55:1 to 1.5:1, such as 1.1:1.

The temperature of the reaction can be 20° C. to 60° C., preferably 45° C. to 55° C., and more preferably 50° C.

The reaction time can be the time that the above-mentioned fused ring pyrimidine compound as shown in formula 1 is no longer react or the above-mentioned fused ring pyrimidine compound as shown in formula 1 is completely consumed by detection (such as TLC), preferably 1 to 26 hours, such as 1 hour.

In the preparation method of the crystal form B of the adipate of fused ring pyrimidine compound as shown in formula 3, after the reaction is completed, the following processing steps can be comprised: cooling the reaction solution to room temperature followed by filtration. The cooling rate is preferably 5° C./h. After the filtration, the operation of washing a resulting filter cake with the mixed solvent can be further comprised. After washing the filter cake, the operation of drying the filter cake can be further comprised; the drying is preferably vacuum drying; and the drying time is preferably 10 hours.

The present disclosure further provides the use of the crystal form A of the fumarate of fused ring pyrimidine compound as shown in formula 2 or the crystal form B of the adipate of fused ring pyrimidine compound as shown in formula 3 in preparing drugs for preventing and/or treating tumors.

Wherein the tumor comprises hematological tumors and solid tumors. The hematological tumors comprise various leukemias, preferably acute myeloid leukemia. The solid tumors can be one or more of colorectal cancer, gastric cancer, liver cancer and lung cancer.

The present disclosure further provides a pharmaceutical composition, which comprises a therapeutically effective amount of the crystal form A of the fumarate of fused ring pyrimidine compound as shown in formula 2, or the crystal form B of the adipate of fused ring pyrimidine compound as shown in formula 3, and a pharmaceutically acceptable carrier.

The content of the crystal form of the salt of the fused ring pyrimidine compound of the present disclosure in the pharmaceutical composition is not particularly limited, and can usually has a mass percentage concentration more than 50%, preferably more than 80%, more preferably more than 90%, and most preferably more than 95%.

In the present disclosure, "crystal form" is not only understood as "crystal type" or "crystal structure"; in a technical solution, "crystal form" is further understood as "a substance having a specific crystal structure" or "a crystal of specific crystal type". For example, in a technical solution, "the crystal form of the fumarate of fused ring pyrimidine compound as shown in formula 2 or the crystal form of the adipate of fused ring pyrimidine compound as shown in formula 3" can be understood as "the fumarate of fused ring pyrimidine compound as shown in formula 2 having a specific crystal structure or the adipate of fused ring pyrimidine compound as shown in formula 3 having a specific crystal structure" or "the crystal form of the fumarate of fused ring pyrimidine compound as shown in formula 2 having a specific crystal type or the crystal form of the adipate of fused ring pyrimidine compound as shown in formula 3 having a specific crystal type".

In the present disclosure, the "crystal forms" are all confirmed by the X-ray powder diffraction characterization as shown.

In the present disclosure, the "anhydride" refers to that the compound contains no more than 1.5% (weight ratio), or no more than 1% (weight ratio) of water, as measured by Karl Fischer (KF) titration method, and combined with TGA test results.

In the present disclosure, the pharmaceutically acceptable carrier refers to the conventional pharmaceutical carrier in the field of pharmacy, preferably comprising one or more of diluents, lubricants, excipients, adhesives, fillers and disintegrating agents.

In the present disclosure, according to the therapeutic purpose, the pharmaceutical composition can be made into various types of unit dosage forms, such as tablets, pills, powders, liquids, emulsions, suspensions, granules, capsules, suppositories and injections (solutions and suspensions), etc.

On the basis of not departing from common knowledge in the art, the above-mentioned various preferred conditions can be combined in any manner, such that various preferred examples of the present disclosure are obtained.

The reagents and raw materials used in the present disclosure are commercially available.

The present disclosure has the positive improvement effects as follows: as compared to the fused ring pyrimidine compound as shown in formula 1 in the prior art, the salt of the fused ring pyrimidine compound and the crystal form of the salt of the fused ring pyrimidine compound provided shows at least one of the following advantages: a better stability, not easily absorbing moisture, being of a polycrystalline type, having a chemical stability and pharmacokinetics, and having an improved solubility.

DETAILED DESCRIPTION OF THE EMBODIMENT

Figure 1:
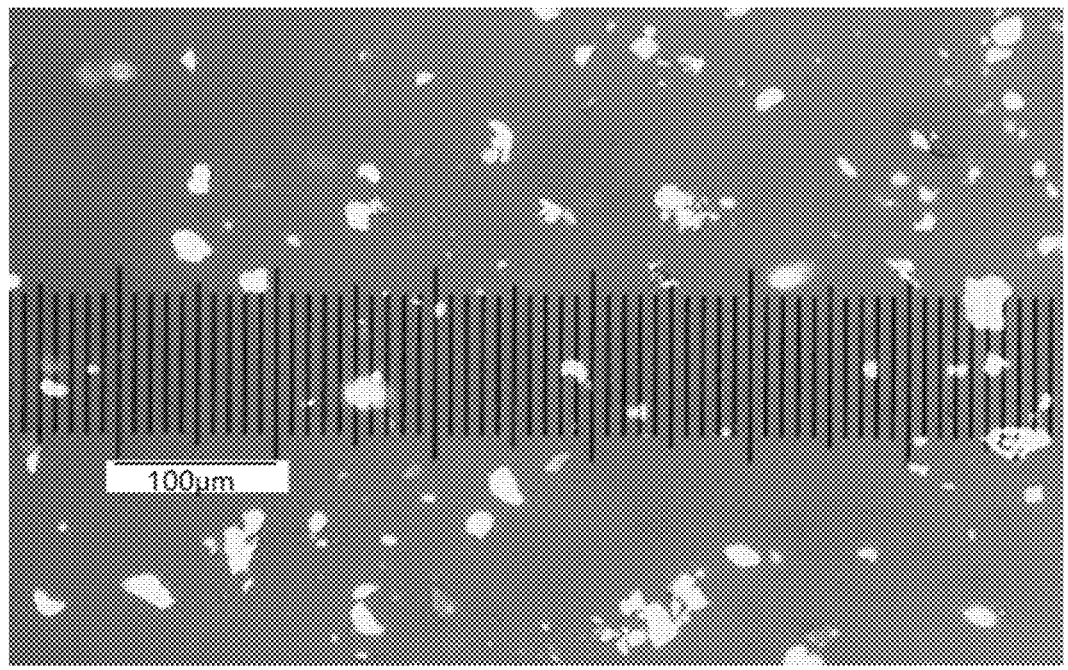
FIG. 1 is the polarized light micrograph of the crystal form A of the fumarate of fused ring pyrimidine compound as shown in formula 2.

The present disclosure is further illustrated by the following example, but the present disclosure is not limited thereto. Experimental methods with specific conditions are not indicated in the following examples, but can be chosen according to conventional methods and conditions or commodity instructions.

Example 1 Preparation of the Fumarate of Fused Ring Pyrimidine Compound as Shown in Formula 2

100 mg (0.228 mmol, 1 eq) of compound N-[7-(4-fluoro-2-methoxyphenyl)-6-methylthieno[3,2-d]pyrimidin-2-yl]-1-(piperidin-4-yl)-1H-pyrazol-4-amine (synthetized according to patent CN 106366093 A example 31) was weighed into a vial, 10 mL of 88% of acetone-water solution was added to the vial at about 50° C. and stirred to clear. 1.1 mL of a solution of fumaric acid in ethanol with a concentration of 0.25 mol/L (0.275 mmol, 1.2 eq) was slowly dropwise added to a solution of the free base of the fused ring pyrimidine compound, stirred and reacted at 50° C. for 1 hour, then the solution was slowly cooled to room temperature at a rate of 5° C./h, the solid was collected and dried under vacuum at 40° C. overnight.

$^1$H-NMR (400 MHz, DMSO-$d_6$) δ: 9.45 (s, 1H), 8.94 (s, 1H), 7.75 (s, 1H), 7.78-7.33 (m, 2H), 7.15 (d, J=6.4 Hz, 1H), 6.99 (dd, J=7.6 Hz, J=7.2 Hz, 1H), 6.42 (s, 1H), 4.10 (m, 1H), 3.73 (s, 3H), 3.17 (d, J=12.4 Hz, 2H), 2.77 (dd, J=12.4 Hz, J=11.6 Hz, 2H), 2.40 (s, 3H), 1.94 (d, J=11.6 Hz, 2H), 1.73 (m, 2H) ppm.

Example 2 Preparation of the Adipate of Fused Ring Pyrimidine Compound as Shown in Formula 3

The adipate of fused ring pyrimidine compound as shown in formula 3 was prepared according to the preparation method of example 1.

$^1$H-NMR (400 MHz, DMSO-$d_6$) δ: 9.44 (s, 1H), 8.94 (s, 1H), 7.75 (s, 1H), 7.34 (m, 2H), 7.14 (d, J=9.6 Hz, 1H), 6.98 (dd, J=8.0 Hz, J=7.2 Hz, 1H), 3.98 (m, 1H), 3.74 (s, 3H), 3.04 (d, J=12.4 Hz, 2H), 2.58 (dd, J=12.4 Hz, J=10.4 Hz, 2H), 2.40 (s, 3H), 2.17 (m, 2H), 1.84 (d, J=11.6 Hz, 2H), 1.57-1.54 (m, 2H), 1.50-1.48 (m, 2H) ppm.

Example 3 Preparation of the Phosphate of Fused Ring Pyrimidine Compound as Shown in Formula 4

The phosphate of fused ring pyrimidine compound as shown in formula 4 was prepared according to the preparation method of example 1.

$^1$H-NMR (400 MHz, DMSO-$d_6$) δ: 9.47 (s, 1H), 8.94 (s, 1H), 7.74 (s, 1H), 7.72-7.33 (m, 2H), 7.16 (d, J=11.6 Hz, 1H), 6.99 (m, 1H), 4.13 (m, 1H), 3.74 (s, 3H), 3.22 (d, J=12.4 Hz, 2H), 2.83 (dd, J=12.4 Hz, J=11.6 Hz, 2H), 2.40 (s, 3H), 1.86 (m, 2H), 1.76 (m, 2H) ppm.

Example 4 Preparation of the Tartrate of Fused Ring Pyrimidine Compound as Shown in Formula 5

The tartrate of fused ring pyrimidine compound as shown in formula 5 was prepared according to the preparation method of example 1.

$^1$H-NMR (400 MHz, DMSO-$d_6$) δ: 9.46 (s, 1H), 8.95 (s, 1H), 7.75 (s, 1H), 7.40 (s, 1H), 7.37-7.33 (m, 1H), 7.15 (d, J=10.8 Hz, 1H), 6.96-7.00 (m, 1H), 4.13 (m, 1H), 3.82 (s, 1H), 3.70 (s, 3H), 3.22 (d, J=12.4 Hz, 2H), 2.83 (dd, J=12.4 Hz, J=11.6 Hz, 2H), 2.40 (s, 3H), 1.98 (d, J=11.4 Hz, 2H), 1.76 (m, 2H) ppm.

Example 5: Preparation of the Hydrochloride of the Fused Ring Pyrimidine Compound 100 mg (0.228 mmol, 1 eq) of compound N-[7-(4-fluoro-2-methoxyphenyl)-6-methylthieno[3,2-d]pyrimidin-2-yl]-1-(piperidin-4-yl)-1H-pyrazol-4-amine (synthetized according to patent CN 106366093 A example 31) was weighed into a vial, 10 mL of 88% of acetone-water solution was added to the vial at about 50° C. and stirred to clear. 1.1 mL of a solution of hydrochloric acid in ethanol with a concentration of 0.25 mol/L (0.275 mmol, 1.2 eq) was slowly dropwise added to a solution of the free base of the fused ring pyrimidine compound, stirred and reacted at 50° C. for 1 hour, then the solution was slowly cooled to room temperature at a rate of 5° C./h, with no a solid precipitated.

TABLE 4

$^1$HNMR characterization results of the salts of the fused ring pyrimidine compound

| Examples | Identification of molar ratio of compounds to acids in salts by $^1$HNMR |
|---|---|
| Example 1 | Fused ring pyrimidine compound:fumaric acid = 2:1 |
| Example 2 | Fused ring pyrimidine compound:adipic acid = 2:1 |
| Example 3 | Fused ring pyrimidine compound:phosphoric acid = 1:1 |
| Example 4 | Fused ring pyrimidine compound:tartaric acid = 2:1 |

Example 6 Solubility Test of the Salts of the Fused Ring Pyrimidine Compound 2.0 mg of sample was precisely weighed into a liquid phase vial, 1.0 mL of purified water was added, the vial was subjected to ultrasonic treatment for about 30 seconds to disperse the samples evenly, then the vial was placed on a Labquaker rotator, and slowly rotated at room temperature for balancing. After balancing for about 20 hours, each vial was removed, and the solution was filtered with 0.45 μm nylon filter membrane. The filtrate was diluted by DMSO or not diluted and then detected by HPLC. At the same time, two parts of fused ring pyrimidine compounds were weighed and dissolved in DMSO to make standard solutions with concentration of 250 μg/mL and 500 μg/mL, respectively. The standard solutions were subjected to the HPLC detection. The sample concentration vs the peak area of HPLC principal component was used for make a standard curve, and the solubility of each sample in pure water was calculated by a external standard method. Specific results are as shown in Table 5.

TABLE 5

Solubility of the salts of the fused ring
pyrimidine compounds in pure water

| Sample | saturated solubility (mg/mL) |
|---|---|
| Example 1 | 0.17 |
| Example 2 | 0.52 |
| Example 3 | 0.675 |
| Example 4 | 0.146 |
| The fused ring pyrimidine compound as shown in formula 1 | <0.001 |

It can be seen from the above table that solubility of the fumarate, adipate, phosphate and tartrate of the fused ring pyrimidine compound in pure water was significantly improved compared with the free base of the fused ring pyrimidine compound.

Example 7 Preparation of the Crystal Form A of the Fumarate of Fused Ring Pyrimidine Compound as Shown in Formula 2

The fused ring pyrimidine compound as shown in formula 1 (synthetized according to patent CN 106366093 A Example 31) (3.0 g, 6.84 mmol) was dissolved in 88% of acetone-water solution (150 mL), and stirred until clear. The solution was heated to 50±5° C., a solution of fumaric acid (0.437 g, 3.76 mmol) in ethanol (30 mL) was added dropwise, and stirring was continued for 20 h. Then after cooling to room temperature slowly at a rate of 5° C./h under stirring, a solid was generated and filtered, the filter cake was washed with 88% of acetone-water solution (5 mL), dried under vacuum at 50° C. for 18 hours to give a light yellow powdery solid (2.97 g, 87.6% yield).

$^1$H-NMR (400 MHz, DMSO-$d_6$) δ: 9.45 (s, 1H), 8.94 (s, 1H), 7.75 (s, 1H), 7.78-7.33 (m, 2H), 7.15 (d, J=6.4 Hz, 1H), 6.99 (dd, J=7.6 Hz, J=7.2 Hz, 1H), 6.42 (s, 1H), 4.10 (m, 1H), 3.73 (s, 3H), 3.17 (d, J=12.4 Hz, 2H), 2.77 (dd, J=12.4 Hz, J=11.6 Hz, 2H), 2.40 (s, 3H), 1.94 (d, J=11.6 Hz, 2H), 1.73 (m, 2H) ppm.

Example 8 Preparation of the Crystal Form a of the Fumarate of Fused Ring Pyrimidine Compound as Shown in Formula 2

Compound N-[7-(4-fluoro-2-methoxyphenyl)-6-methyl-thieno[3,2-d]pyrimidin-2-yl]-1-(piperidin-4-yl)-1H-pyrazol-4-amine (synthetized according to patent CN 106366093 A example 31) (1.0 eq) was dissolved in 76% of acetone-water solution (mass fraction) and stirred until clear. The solution was heated to 50±5° C., a solution of fumaric acid (1.1 eq, dissolved in ethanol, 0.25 mol/L) in ethanol (30 mL) was added dropwise, and stirring was continued for 20 h. Then after cooling to room temperature slowly at a rate of 5° C./h under stirring, a solid was generated and filtered, the filter cake was washed with 76% of acetone-water solution (5 mL), dried under vacuum at 50° C. for 18 hours to give a light yellow powdery solid (21.2% yield).

Example 9 Preparation of the Crystal Form A of the Fumarate of Fused Ring Pyrimidine Compound as Shown in Formula 2

Compound N-[7-(4-fluoro-2-methoxyphenyl)-6-methyl-thieno[3,2-d]pyrimidin-2-yl]-1-(piperidin-4-yl)-1H-pyrazol-4-amine (synthetized according to patent CN 106366093 A example 31) (1.0 eq) was dissolved in 88% of tetrahydrofuran-water solution (mass fraction) and stirred until clear. The solution was heated to 50±5° C., a solution of fumaric acid (1.1 eq, dissolved in ethanol, 0.25 mol/L) in ethanol (30 mL) was added dropwise, and stirring was continued for 20 h. Then after cooling to room temperature slowly at a rate of 5° C./h, a solid was generated and filtered, the filter cake was washed with 88% of tetrahydrofuran-water solution (5 mL), dried under vacuum at 50° C. for 18 hours to give a light yellow powdery solid (49.6% yield).

Example 10 Preparation of the Crystal Form B of the Adipate of Fused Ring Pyrimidine Compound as Shown in Formula 3

The fused ring pyrimidine compound as shown in formula 1 (synthetized according to patent CN 106366093 A Example 31) (1 g, 2.28 mmol) was dissolved in 88% of acetone-water solution (100 mL), and stirred until clear. The solution was heated to 50° C., then 10 mL of a solution of adipic acid in ethanol with a concentration of 0.25 mol/L was dropwise added to a solution of the fused ring pyrimidine compound, and stirring was continued for 1 hour. Then after cooling to room temperature slowly at a rate of 5° C./h under stirring, a solid was generated, filtered, and washed with 88% of acetone-water solution (5 mL), and a light yellow powdery solid was obtained after the filter cake was dried under vacuum at 40° C. for 18 hours.

$^1$H-NMR (400 MHz, DMSO-$d_6$) δ: 9.44 (s, 1H), 8.94 (s, 1H), 7.75 (s, 1H), 7.34 (m, 2H), 7.14 (d, J=9.6 Hz, 1H), 6.98 (dd, J=8.0 Hz, J=7.2 Hz, 1H), 3.98 (m, 1H), 3.74 (s, 3H), 3.04 (d, J=12.4 Hz, 2H), 2.58 (dd, J=12.4 Hz, J=10.4 Hz, 2H), 2.40 (s, 3H), 2.17 (m, 2H), 1.84 (d, J=11.6 Hz, 2H), 1.57-1.54 (m, 2H), 1.50-1.48 (m, 2H) ppm.

Example 11 Observation by Polarized Light Microscope

A small amount of the crystal form A of the fumarate of fused ring pyrimidine compound as shown in formula 2 was taken, placed on a glass slide with scale, and dispersed by adding an appropriate amount of liquid paraffin, and the glass slide was covered with a coverslip, and placed under 10× objective lens of the microscope to observe the particle shape, size and crystallization properties. A crossed polorizer was used to observe the birefringent property and crystal habit of the sample, and a digital camera was used to take photos, as shown in FIG. 1.

Figure 6:
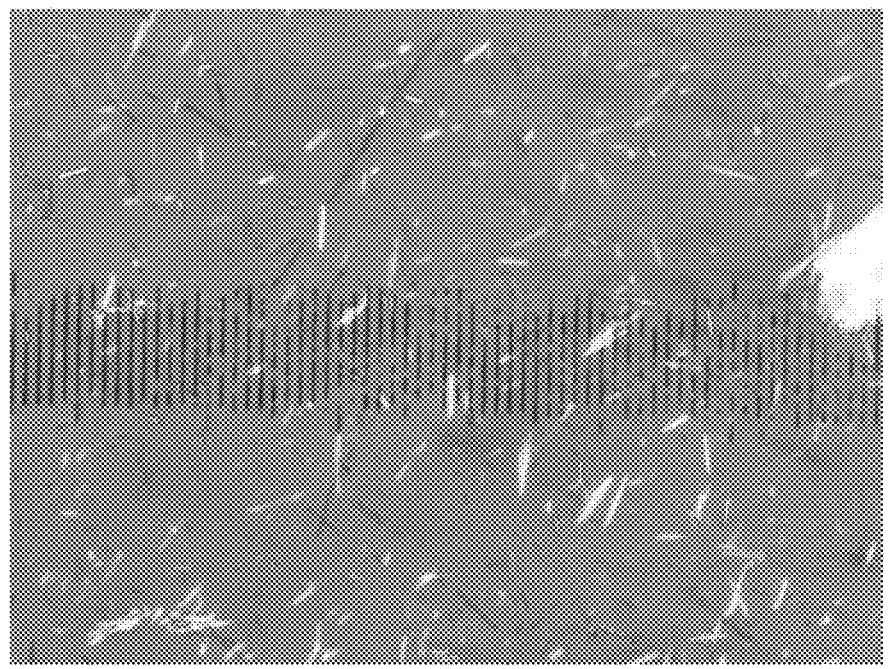
FIG. 6 is the polarized light micrograph of the crystal form B of the adipate of fused ring pyrimidine compound as shown in formula 3.

Polarized light micrographs of the crystal form B of the adipate of fused ring pyrimidine compound as shown in formula 3 is shown in FIG. 6.

Example 12 Solubility Test of the Crystal Form A of the Fumarate of Fused Ring Pyrimidine Compound as Shown in Formula 2 and the Crystal Form B of the Adipate of Fused Ring Pyrimidine Compound as Shown in Formula 3 in a Medium

TABLE 6

Solubility of the crystal form A of the fumarate of and the crystal form B of the adipate of the fused ring pyrimidine compound in a medium

| | Sample name | | | | | |
|---|---|---|---|---|---|---|
| | The crystal form A of the fumarate of fused ring pyrimidine compound as shown in formula 2 | | The crystal form B of the adipate of fused ring pyrimidine compound as shown in formula 3 | | The fused ring pyrimidine compound as shown in formula 1 | |
| Medium | Solubility (calculated by free base of the fused ring pyrimidine compound) | pH value of sample solution for solubility | Solubility (calculated by free base of the fused ring pyrimidine compound) | pH value of sample solution for solubility | Solubility (calculated by free base of the fused ring pyrimidine compound) | pH value of sample solution for solubility |
| pH 4 (50 mM phosphate buffer) | 0.159 | 4.33 | 0.104 | 4.85 | 0.054 | 5.67 |
| pH 6 (50 mM phosphate buffer) | 0.036 | 5.96 | 0.035 | 6.01 | 0.025 | 6.29 |
| Purified water | 0.126 | 7.27 | 0.463 | 7.09 | <0.001 | 8.29 |
| intestinal fluid in simulated fed state (FeSSIF) | 1.906 | 5.19 | 1.46 | 5.2 | 1.469 | 5.27 |

As can be seen from Table 6, the solubility of the crystal form A of the fumarate of fused ring pyrimidine compound as shown in formula 2 and the crystal form B of the adipate of fused ring pyrimidine compound in pure water was significantly improved compared to the solubility of free base of the fused ring pyrimidine compound, and the solubility of the crystal form A of the fumarate of fused ring pyrimidine compound as shown in formula 2 was high in an intestinal fluid (FeSSIF) in simulated fed state.

Example 13 Analysis by X-ray Powder Diffraction (XRPD)

Methods: A suitable amount of samples were taken and spread on a monocrystalline silicon wafer, the XRPD test was carried out at room temperature, and the specific experimental parameters was as follows: the light source was CuK, the X-ray intensity was 40 KV/40 mA, the scanning mode was Theta-theta, the scanning angle range was 4° to 40°, the step length was 0.05° and the scanning speed was 0.5 s/step.

In the X-ray powder diffraction pattern of the crystal form A of the fumarate of fused ring pyrimidine compound as shown in formula 2, the 2θ angles of the characteristic diffraction peaks were respectively (2θ±0.2°): 7.311°, 8.161°, 9.397°, 12.341°, 14.679°, 15.331°, 15.755°, 17.255°, 18.664°, 19.207°, 19.707°, 21.207°, 21.701° and 23.423°. The list of X ray diffraction peak and relative intensity of the crystal form A of the fumarate of fused ring pyrimidine compound as shown in formula 2 was as shown in table 1; and X-ray powder diffraction pattern was as shown in table 2.

In the X-ray powder diffraction pattern of the crystal form B of the adipate of fused ring pyrimidine compound as shown in formula 3, the 2θ angles of the characteristic diffraction peaks were respectively (2θ±0.2°): 5.717°, 6.637°, 1.422°, 13.271°, 15.456°, 16.528°, 19.971°, 20.936°, 23.002° and 26.959°. The list of X ray diffraction peak and relative intensity of the crystal form B of the adipate of fused ring pyrimidine compound as shown in formula 3 was as shown in table 3; and X-ray powder diffraction pattern was as shown in table 7.

Example 14

Thermogravimetic Analysis (TGA)

Figure 3:
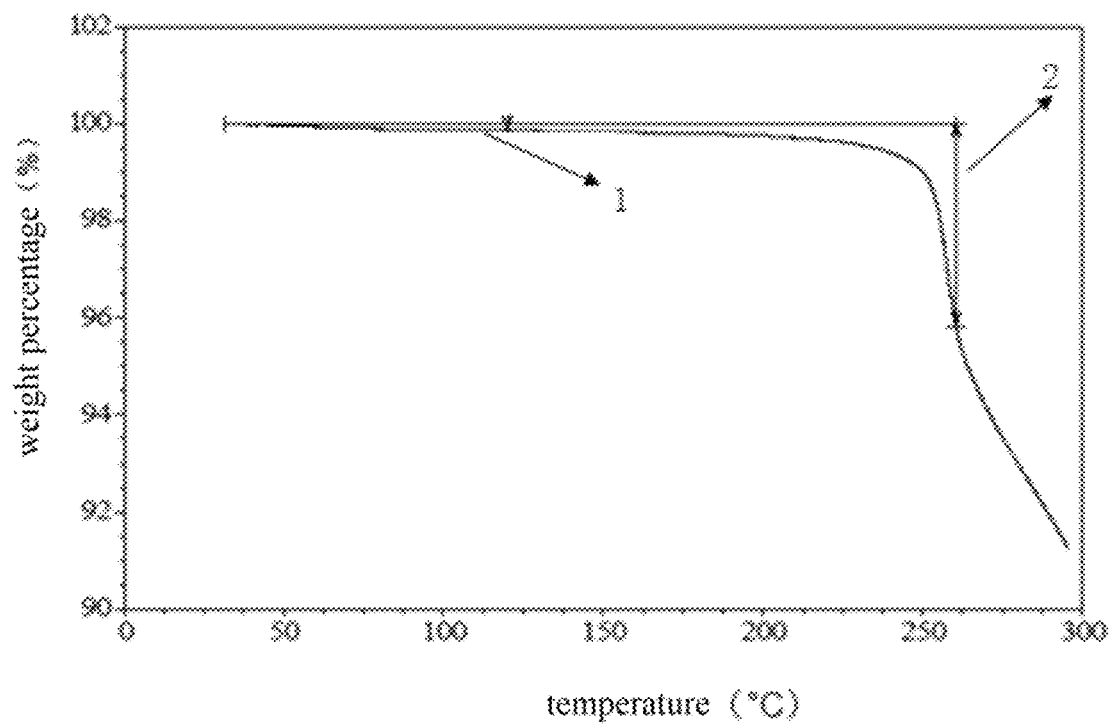
FIG. 3 is the thermogravimetic analysis diagram of the crystal form A of the fumarate of fused ring pyrimidine compound as shown in formula 2, wherein in region 1, 0.1353% weight loss occurs from 31.05° C. to 119.97° C., and the mass for the weight loss thereof is 0.1685 mg; in region 2, 4.161% weight loss occurs from 119.97° C. to 260.83° C., and the mass for the weight loss thereof is 0.5180 mg.

12.4470 mg of the crystal form A of the fumarate of fused ring pyrimidine compound as shown in formula 2 was placed in a platinum sample tray, and heated from 25° C. to 300° C. at a heating rate of 10° C./min under nitrogen flow (50 mL/min) atmosphere, as shown in FIG. 3. 0.1353% weight loss occurred from 31.05° C. to 119.97° C., the mass for the weight loss thereof was 0.1685 mg, and the weight loss herein was a trace amount of solvent on the surface; 4.161% weight loss occurred from 119.97° C. to 260.83° C., and the mass for the weight loss thereof was 0.5180 mg.

Figure 8:
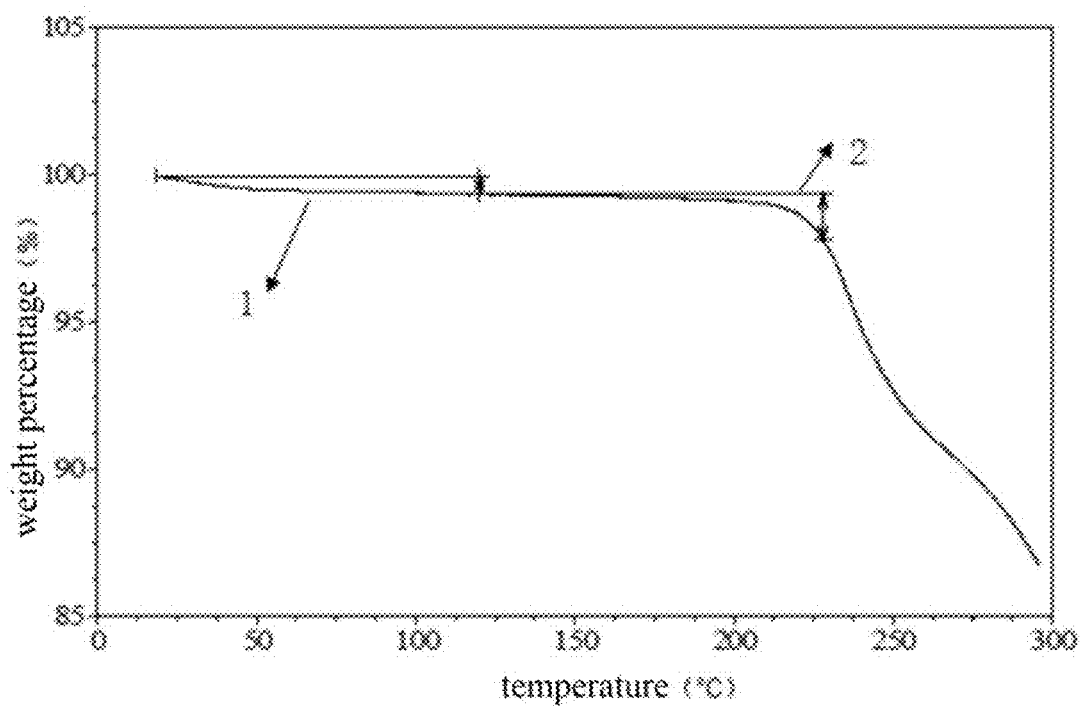
FIG. 8 is the thermogravimetic analysis diagram of the crystal form B of the adipate of fused ring pyrimidine compound as shown in formula 3, wherein in region 1, 0.6249% weight loss occurs from 18.2° C. to 120° C., and the mass for the weight loss thereof is 0.03491 mg; in region 2, 1.567% weight loss occurs from 120° C. to 228° C., and the mass for the weight loss thereof is 0.08752 mg.

5.5870 mg of the crystal form B of the adipate of fused ring pyrimidine compound as shown in formula 3 was placed in a platinum sample tray, and heated from 25° C. to 300° C. at a heating rate of 10° C./min under nitrogen flow (50 mL/min) atmosphere, as shown in FIG. 8. 0.6249% weight loss occurred from 18.2° C. to 120° C., and the mass for the weight loss thereof was 0.03491 mg, which was a trace amount of solvent on the surface; 1.567% weight loss occurred from 120° C. to 228° C., and the mass for the weight loss thereof was 0.08752 mg.

Example 15

Dynamic Vapor Sorption Analysis (DVS)

Figure 4:
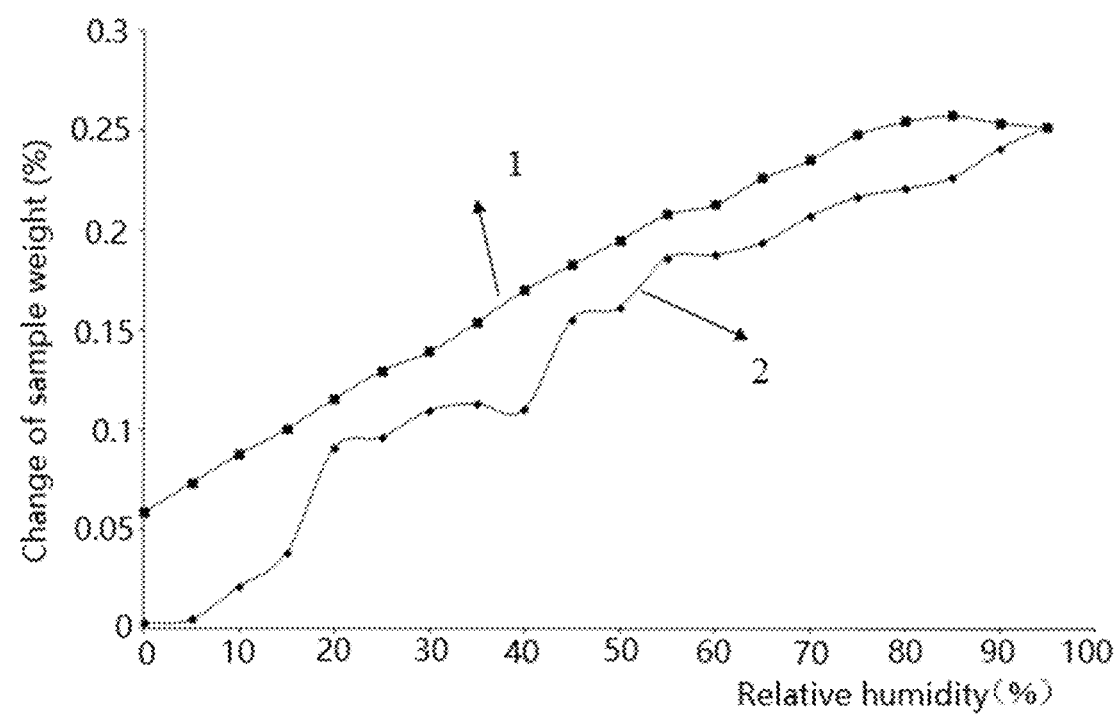
FIG. 4 is the dynamic vapor sorption diagram of the crystal form A of the fumarate of fused ring pyrimidine compound as shown in formula 2, wherein 1 is sorption curve, and 2 is desorption curve.

10 mg of the crystal form A of the fumarate of fused ring pyrimidine compound as shown in formula 2 was weighed, and dried for 60 min under the condition of a temperature of 25° C. and a humidity of 0% RH, and then the humidity absorption characteristic of the sample was tested when the humidity changed from 0% RH to 95% RH, and the dehumidification characteristic of the sample was tested when the humidity changed from 95% RH to 0% RH. Each step length for the humidity changes was 5% RH, the balance standard was that the weight change rate was less than 0.01%/min within 5 min, and the longest balance time was 2 hours. The results showed that the weight gain of the sample from 0% RH to 95% RH was 0.2518%, as shown in FIG. 4.

Figure 9:
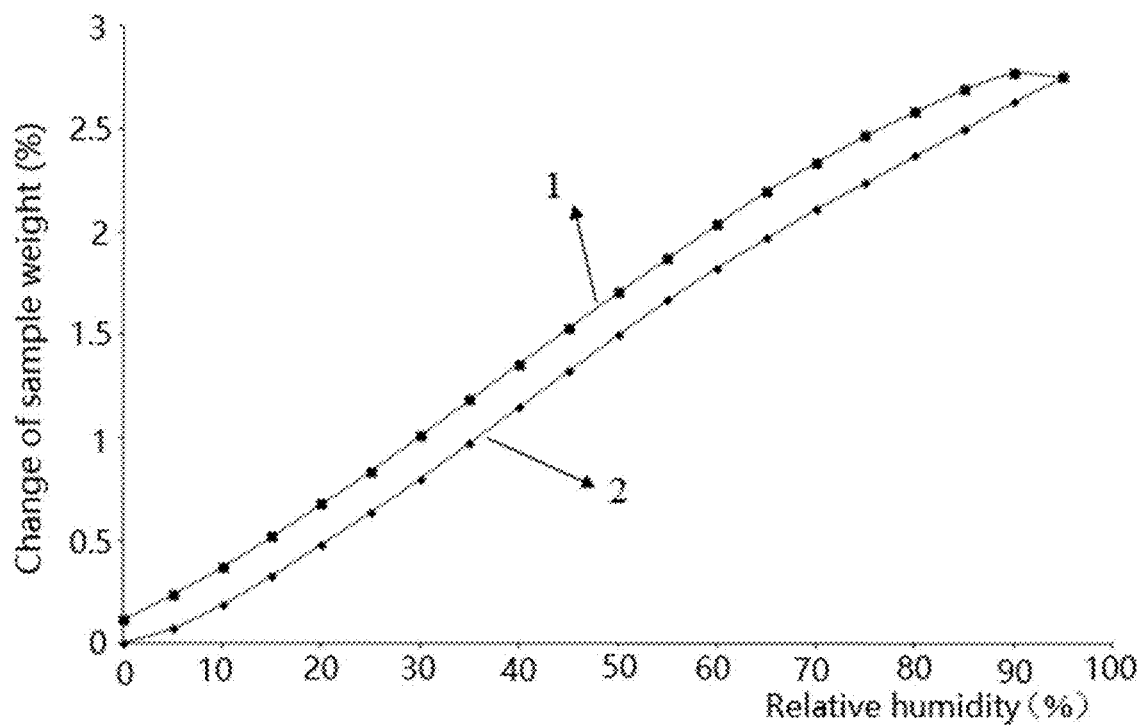
FIG. 9 is the dynamic vapor sorption diagram of the crystal form B of the adipate of fused ring pyrimidine compound as shown in formula 3, wherein 1 is sorption curve, and 2 is desorption curve.

10 mg of the crystal form B of the adipate of fused ring pyrimidine compound as shown in formula 3 was weighed, and dried for 60 min under the condition of a temperature of 25° C. and a humidity of 0% RH, and then the humidity absorption characteristic of the sample was tested when the humidity changed from 0% RH to 95% RH, and the dehumidification characteristic of the sample was tested when the humidity changed from 95% RH to 0% RH. Each step length for the humidity changes was 5% RH, the balance standard was that the weight change rate was less than 0.01%/min within 5 min, and the longest balance time was 2 hours. The results showed that the weight gain of the sample from 0% RH to 95% RH was 2.751%, as shown in FIG. 9.

Figure 5:
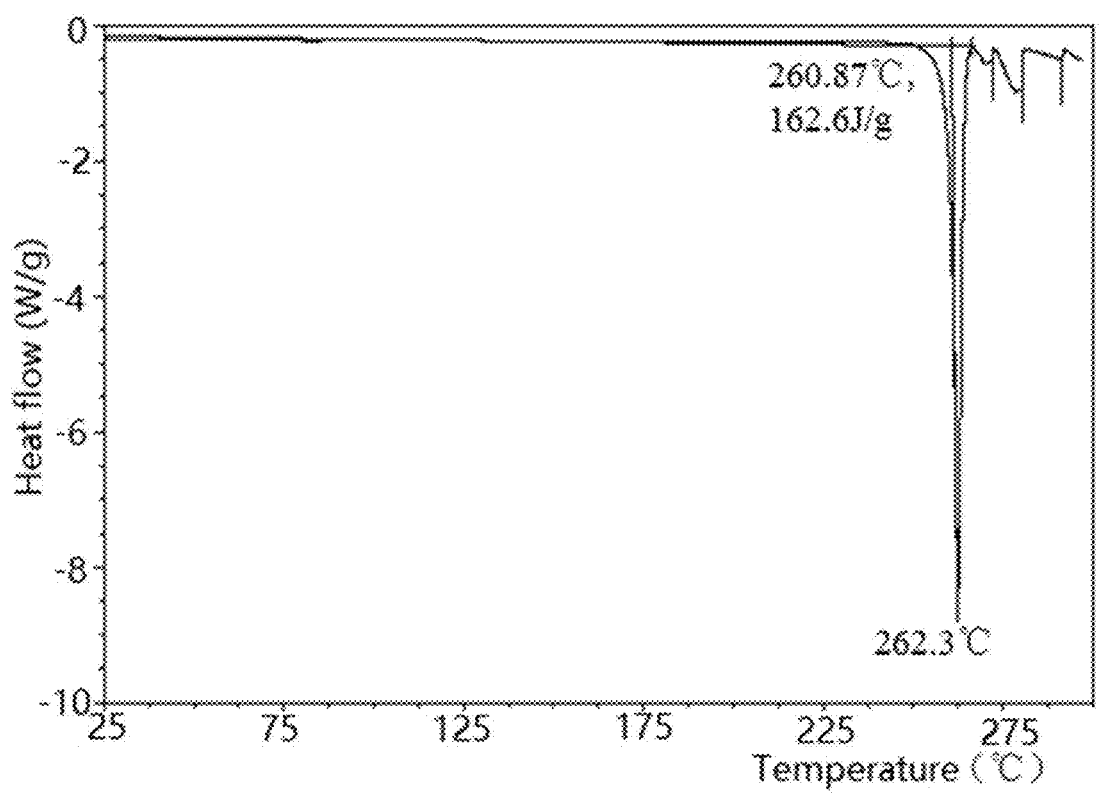
FIG. 5 is the differential scanning calorimetry diagram of the crystal form A of the fumarate of fused ring pyrimidine compound as shown in formula 2.

Dynamic vapor sorption analysis (DVS) for the phosphate and the tartrate referred to the above method and was shown in table 7.

weighed, and placed in a non-sealed aluminum tray, the sample was balanced at 25° C. under nitrogen flow (50 mL/min) atmosphere, then heated from 25° C. to 300° C. at a heating rate of 10° C./min, and the melting heat was 162.6 J/g from a temperature of 260.87° C. to 262.3° C., as shown in FIG. 5.

Figure 10:
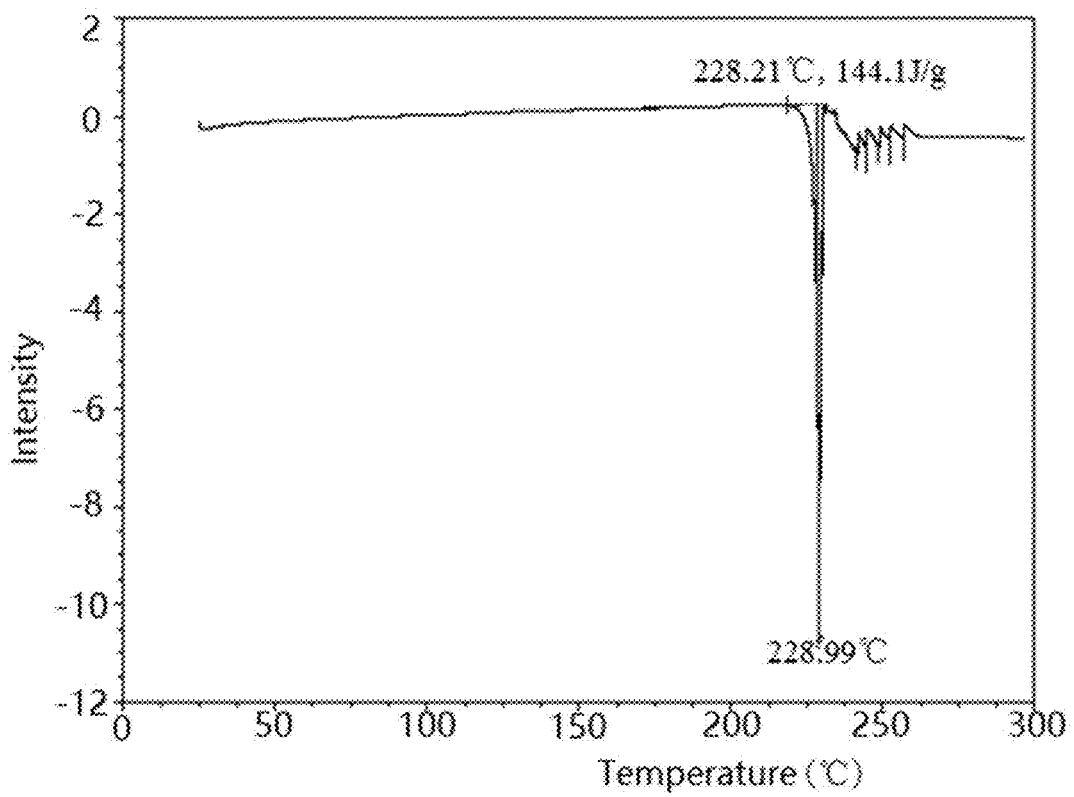
FIG. 10 is the differential scanning calorimetry diagram of the crystal form B of the adipate of fused ring pyrimidine compound as shown in formula 3.

2.3040 mg of the crystal form B of the adipate of fused ring pyrimidine compound as shown in formula 3 was weighed, and placed in a non-sealed aluminum tray, the sample was balanced at 25° C. under nitrogen flow (50 mL/min) atmosphere, then heated from 25° C. to 300° C. at a heating rate of 10° C./min, and the melting heat was 144.1 J/g at a temperature from 228.21° C. to 228.99° C., as shown in FIG. 10.

Example 17 Stability Test

The crystal form A of the fumarate of fused ring pyrimidine compound as shown in formula 2, the crystal form B of the adipate of fused ring pyrimidine compound as shown in formula 3 and the fused ring pyrimidine compound as shown in formula 1 were subjected to tests at a high temperature of 60° C., 25° C./60% RH, 40° C./75% RH and highlight

TABLE 7

| Dynamic vapor sorption analysis (DVS) characterization | | | | | |
|---|---|---|---|---|---|
| Name | DSC | ¹HNMR | DVS | XRPD of samples after DVS test | Salt type definition |
| The fumarate of fused ring pyrimidine compound as shown in formula 2 | Melting point of 258.36° C. | Free base:fumaric acid = 2:1 | Weight loss in drying stage: 0.117% Moisture-absorption weight gain at 85% RH: 0.324% Moisture-absorption weight gain at 95% RH: 0.404% | XRPD diffraction peaks were consistent before and after DVS test | Hemifumarate, anhydride |
| The adipate of fused ring pyrimidine compound as shown in formula 3 | Melting point of 207.84° C. | Free base:adipic acid = 2:1 | Not Tested | Not Tested | Hemiadipate, anhydride |
| The phosphate of fused ring pyrimidine compound as shown in formula 4 | Melting point of 269.10° C., a very wide melting range, may be a mixed crystal | Free base:phosphoric acid =1:1 | Weight loss in drying stage: 0.752% Moisture-absorption weight gain at 85% RH: 6.95% Moisture-absorption weight gain at 95% RH: 12.15% | XRPD diffraction peaks were consistent before and after DVS test | Monophosphate, anhydride |
| The tartrate of fused ring pyrimidine compound as shown in formula 5 | Two large endothermic peaks and one exothermic peak appeared on DSC, onset temperatures of the endothermic peaks were 52.58° C. and 240.34° C., respectively, and the onset temperature of the exothermic peak was 87.25° C. | Free base:tartaric acid = 2:1 | Weight loss in drying stage: 5.88% Moisture-absorption weight gain at 85% RH: 8.390% Moisture-absorption weight gain at 95% RH: 8.659% | XRPD diffraction peaks were not consistent before and after DVS test | Hemitartrate, hydrate |

Example 16 Differential Scanning Calorimetry Analysis (DSC)

2.6680 mg of the crystal form A of the fumarate of fused ring pyrimidine compound as shown in formula 2 was irradiation (4500 lx±500 lx), the test time was 20 days, the sample bottles were placed under different test conditions, and samples were taken at 0 and 20 days to detect the total amount of impurities, and the test results were shown in Table 8 below.

TABLE 8

Stability test results

| Impurity content: (%) Test items | | | The crystal form A of the fumarate of fused ring pyrimidine compound as shown in formula 2 | The crystal form B of the adipate of fused ring pyrimidine compound as shown in formula 3 | The fused ring pyrimidine compound as shown in formula 1 |
|---|---|---|---|---|---|
| | Time point | Condition | | | |
| | Day 0 | / | 0.25 | 0.24 | 1.44 |
| | Day 20 | 60° C | 0.25 | 0.23 | 1.44 |
| | | 25° C/60% RH | 0.25 | 0.22 | 1.46 |
| | | 40° C/75% RH | 0.28 | 0.22 | 1.49 |
| | | Light | 0.46 | 0.42 | 2.06 |

It can be seen that, in the condition of high temperature and high humidity, the crystal form A of the fumarate of fused ring pyrimidine compound as shown in formula 2, the crystal form B of the adipate of fused ring pyrimidine compound as shown in formula 3 and the fused ring pyrimidine compound as shown in formula 1 of the present disclosure all exhibited good chemical stability, but under light conditions, the stability of the crystal form A of the fumarate of fused ring pyrimidine compound as shown in formula 2 and the crystal form B of the adipate of fused ring pyrimidine compound as shown in formula 3 of the present disclosure was significantly higher than that of the fused ring pyrimidine compound as shown in formula 1.

Example 18 Pharmacokinetic Experiments

1) Preparation of animals 9 healthy male SD rats, each with a body weight of 220-230 g, were taken, fed with standard formulated granulated feed for rats at fixed times every day, and fasted for 12 hours before the experiment, and feeding was resumed after 4 hours of administration. Rats were free to drink water before, after and during the experiment. 9 rats were randomly divided into 3 groups.

2) Formulation of drugs: The fused ring pyrimidine compound as shown in formula 1, the crystal form A of the fumarate of fused ring pyrimidine compound as shown in formula 2 and the crystal form B of the adipate of fused ring pyrimidine compound as shown in formula 3 were accurately weighed, and were formulated into a 1 mg/mL solution in water (Wahaha/111830) with 0.5% MC (Fluka/BCBK3534K) and 0.5% Tween80 (TCl/V4FSC), respectively.

3) Intragastric administration with single dose (10 mg/kg): in the first group, rats were intragastrically administered with a solution of the fused ring pyrimidine compound as shown in formula 1, in the second group, rats were intragastrically administered with a solution of the crystal form A of the fumarate of fused ring pyrimidine compound as shown in formula 2, and in the third group, rats were intragastrically administered with a solution of the crystal form B of the adipate of fused ring pyrimidine compound as shown in formula 3.

4) Collection of blood samples: About 150 μL of blood was taken from the fundus venous plexus before administration and 0.083, 0.25, 0.5, 1, 2, 4, 8 and 24 hours after administration from each rat in the three groups, and anticoagulated with $K_2EDTA$, plasma was separated by centrifugation and the supernatant was collected for LC-MS analysis.

Experimental results: See table 9.

TABLE 9

Results of blood drug concentration after intragastric administration to rats

| Compounds | Blood drug concentration (AUC, ng/mL · h) |
|---|---|
| The fused ring pyrimidine compound as shown in formula 1 | 57.7 |
| The crystal form A of the fumarate of fused ring pyrimidine compound as shown in formula 2 | 999 |
| The crystal form B of the adipate of fused ring pyrimidine compound as shown in formula 3 | 1038 |

It can be seen that, in the single dose (10 mg/kg) intragastric administration experiment of rats, the blood drug concentration of the crystal form A of the fumarate of fused ring pyrimidine compound as shown in formula 2 and the crystal form B of the adipate of fused ring pyrimidine compound as shown in formula 3 of the present disclosure was more than 17 times the blood drug concentration of the fused ring pyrimidine compound as shown in formula 1.

What is claimed is:

1. A crystal form A of a fumarate of fused ring pyrimidine compound as shown in formula 2, wherein X-ray powder diffraction pattern of the crystal form A represented by diffraction angle 2θ values has characteristic peaks at 7.311°, 8.161°, 9.397°, 12.341°, 14.679°, 15.331°, 15.755°, 17.255°, 18.664°, 19.207°, 19.707°, 21.207°, 21.701° and 23.423°,

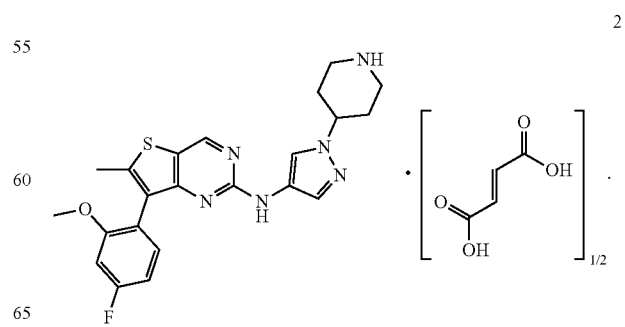

Figure 2:
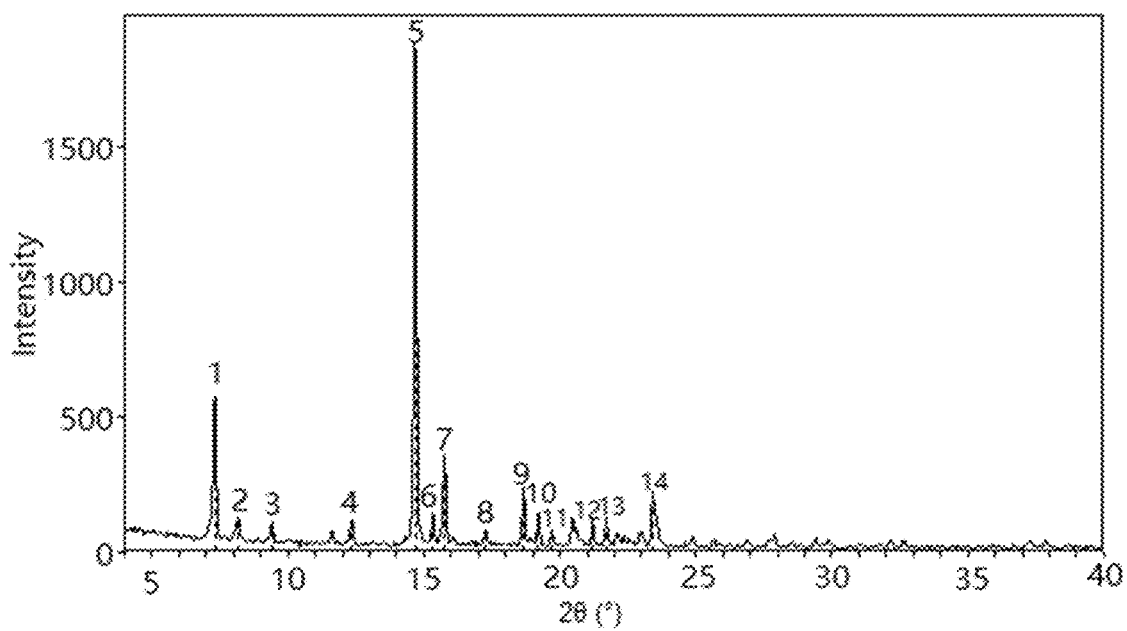
FIG. 2 is the X-ray powder diffraction pattern of the crystal form A of the fumarate of fused ring pyrimidine compound as shown in formula 2.

2. The crystal form A of the fumarate of fused ring pyrimidine compound as shown in formula 2 as defined in claim 1, wherein X-ray diffraction characteristic peaks and relative intensities are shown in the table below:

| No. | 2θ(2θ ± 0.2°) | Relative intensity % |
|---|---|---|
| 1 | 7.311 | 27.6 |
| 2 | 8.161 | 3.7 |
| 3 | 9.397 | 3.7 |
| 4 | 12.341 | 4.8 |
| 5 | 14.679 | 100 |
| 6 | 15.331 | 5.1 |
| 7 | 15.755 | 17.4 |
| 8 | 17.255 | 2.8 |
| 9 | 18.664 | 11.2 |
| 10 | 19.207 | 6.1 |
| 11 | 19.707 | 2.9 |
| 12 | 21.207 | 4.3 |
| 13 | 21.701 | 4.5 |
| 14 | 23.423 | 11 | or, the X-ray powder diffraction pattern of the crystal form A of the fumarate of fused ring pyrimidine compound as shown in formula 2 is as shown in FIG. 2;

or, the characteristic absorption peaks and intensities in infrared absorption spectrum diagram of the crystal form A of the fumarate of fused ring pyrimidine compound as shown in formula 2 are shown in the table below;

| No. | Absorption peak wave number (cm$^{-1}$) | Intensity % |
|---|---|---|
| 1 | 3284 | 95.15 |
| 2 | 3005 | 96.93 |
| 3 | 2962 | 89.56 |
| 4 | 2933 | 93.43 |
| 5 | 1624 | 73.28 |
| 6 | 1606 | 57.47 |
| 7 | 1595 | 47.01 |
| 8 | 1560 | 27.7 |
| 9 | 1492 | 62.77 |
| 10 | 1408 | 32.96 |
| 11 | 1352 | 39.55 |
| 12 | 663 | 62.49 | or, in the thermogravimetic analysis of the crystal form A of the fumarate of fused ring pyrimidine compound as shown in formula 2, 0.1353% weight loss occurs from 31.05° C. to 119.97° C.; 4.161% weight loss occurs from 119.97° C. to 260.83° C.;

or, in the dynamic vapor sorption of the crystal form A of the fumarate of fused ring pyrimidine compound as shown in formula 2, the weight gain is 0.2518% in the range of 0% to 95% relative humidity;

or, in the differential scanning calorimetry of the crystal form A of the fumarate of fused ring pyrimidine compound as shown in formula 2, an absorption peak occurs at 262° C.±5° C., and the melting heat is 162.6 J/g;

or, the differential scanning calorimetry of the crystal form A of the fumarate of fused ring pyrimidine compound as shown in formula 2 is as shown in FIG. 5;

or, the crystal form A of the fumarate of fused ring pyrimidine compound as shown in formula 2 is an anhydride.

3. A pharmaceutical composition, comprising a therapeutically effective amount of the crystal form A of the fumarate of fused ring pyrimidine compound as shown in formula 2 as defined in claim 1, and a pharmaceutically acceptable carrier.

4. A preparation method for the crystal form A of the fumarate of fused ring pyrimidine compound as shown in formula 2 as defined in claim 1, wherein the preparation method comprises the following steps: reacting an alcoholic solution of fumaric acid with a mixture of the fused ring pyrimidine compound as shown in formula 1 and a mixed solvent; wherein the mixed solvent is one of a mixed solvent of ketone and water, a mixed solvent of alcohol and water, and a mixed solvent of ether and water;

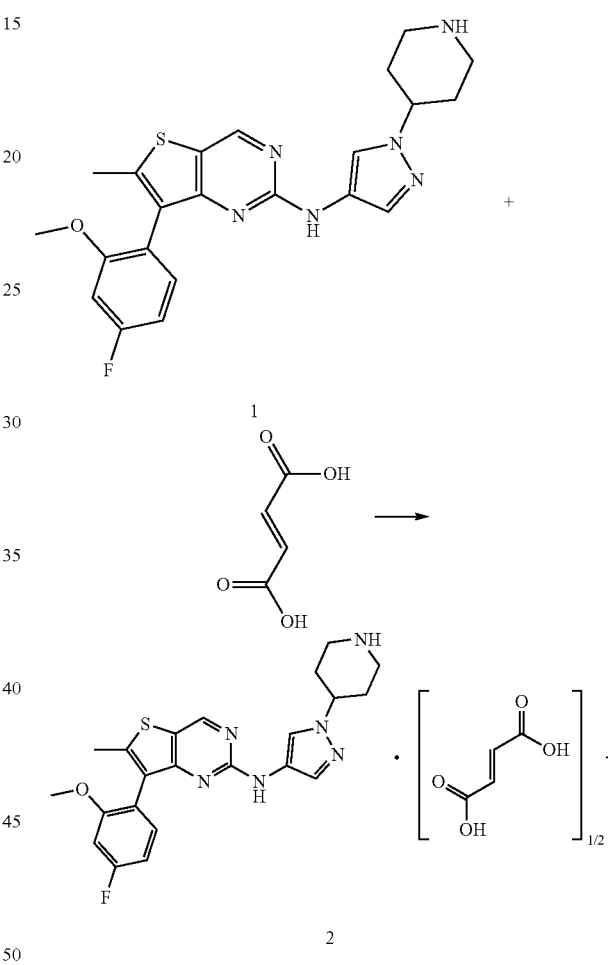

5. The preparation method as defined in claim 4, wherein the reaction is performed by dropwise adding the alcoholic solution of fumaric acid into the solution of the fused ring pyrimidine compound as shown in formula 1 and the mixed solvent for reaction;

or, the mixing method of the fused ring pyrimidine compound as shown in formula 1 and the mixed solvent is to add the fused ring pyrimidine compound as shown in formula 1 into the mixed solvent;

or, the alcoholic solution of fumaric acid is methanol solution of fumaric acid or ethanol solution of fumaric acid;

or, the mixed solvent is one of a mixed solvent of acetone and water, a mixed solvent of methanol or ethanol and water, and a mixed solvent of tetrahydrofuran and water;

or, the molar concentration of the alcoholic solution of fumaric acid is 0.100 mol/L to 0.500 mol/L;

or, the volume-to-mass ratio of the volume of the mixed solvent to the mass of the fused ring pyrimidine compound as shown in formula 1 is 40 mL/g to 110 mL/g;

or, the molar ratio of the fumaric acid to the fused ring pyrimidine compound as shown in formula 1 is 0.5:1 to 3:1;

or, the temperature of the reaction is 20° C. to 60° C.;

or, the reaction time is 1 to 26 hours;

or, in the preparation method of the crystal form A of the fumarate of fused ring pyrimidine compound as shown in formula 2, after the reaction is completed, the following processing steps are comprised:

cooling the reaction solution to room temperature, followed by filtration;

after the filtration, washing the resulting filter cake with the mixed solvent; and after washing the filter cake, drying the filter cake.

6. The preparation method as defined in claim 5, wherein the mixed solvent is one of a mixed solvent of acetone with 78% to 88% mass percentage concentration and water, a mixed solvent of methanol or ethanol with 90% mass percentage concentration and water, and a mixed solvent of tetrahydrofuran with 88% mass percentage concentration and water;

or, the molar concentration of the alcoholic solution of fumaric acid is 0.125 mol/L to 0.250 mol/L;

or, the volume-to-mass ratio of the volume of the mixed solvent to the mass of the fused ring pyrimidine compound as shown in formula 1 is 50 mL/g to 100 mL/g;

or, the molar ratio of the fumaric acid to the fused ring pyrimidine compound as shown in formula 1 is 0.55:1 to 1.1:1;

or, the temperature of the reaction is 45° C. to 55° C.;

or, the cooling rate is 5° C./h;

or, the drying is vacuum drying.

7. A method for treating a tumor in a subject in need thereof, comprising administering a therapeutically effective amount of the crystal form A of the fumarate of fused ring pyrimidine compound as shown in formula 2 as defined in claim 1 to the subject, wherein the tumor is selected from the group consisting of hematological tumors, colorectal cancer, gastric cancer, liver cancer and lung cancer.

8. The method as defined in claim 7, wherein the hematological tumors comprise leukemia.

9. The method as defined in claim 8, wherein the leukemia is acute myeloid leukemia.

Figure 7:
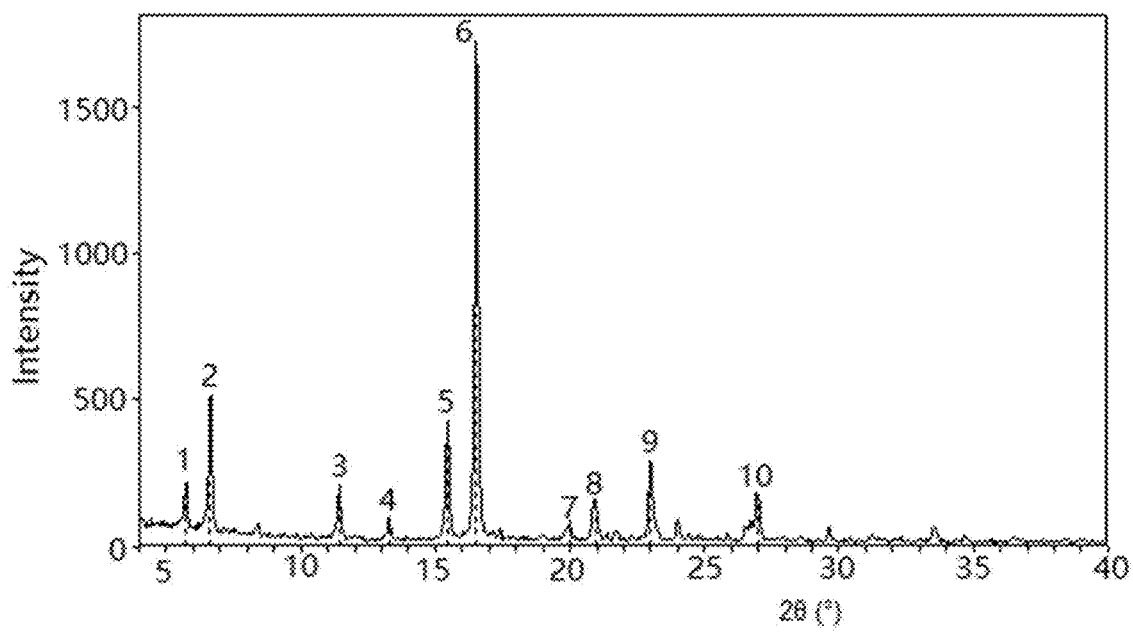
FIG. 7 is the X-ray powder diffraction pattern of the crystal form B of the adipate of fused ring pyrimidine compound as shown in formula 3.

10. A crystal form B of an adipate of fused ring pyrimidine compound as shown in formula 3, wherein X-ray powder diffraction pattern of the crystal form B represented by diffraction angle 2θ values has characteristic peaks at 5.717°, 6.637°, 11.422°, 13.271°, 15.456°, 16.528°, 19.971°, 20.936°, 23.002° and 26.959°;

11. The crystal form B of the adipate of fused ring pyrimidine compound as shown in formula 3 as defined in claim 10, wherein X-ray diffraction characteristic peaks and relative intensities are shown in the table below:

| No. | 2θ(2θ ± 0.2°) | Relative intensity % |
| --- | --- | --- |
| 1 | 5.717 | 8.9 |
| 2 | 6.637 | 23.8 |
| 3 | 11.422 | 11.7 |
| 4 | 13.271 | 3.9 |
| 5 | 15.456 | 21.5 |
| 6 | 16.528 | 100 |
| 7 | 19.971 | 3.5 |
| 8 | 20.936 | 8.9 |
| 9 | 23.002 | 18.2 |
| 10 | 26.959 | 17.2 | or, the X-ray powder diffraction pattern of the crystal form B of the adipate of fused ring pyrimidine compound as shown in formula 3 is as shown in FIG. 7;

or, in the thermogravimetic analysis of the crystal form B of the adipate of fused ring pyrimidine compound as shown in formula 3, 0.6249% weight loss occurs from 18.2° C. to 120° C.; 1.567% weight loss occurs from 120° C. to 228° C.;

or, in the dynamic vapor sorption of the crystal form B of the adipate of fused ring pyrimidine compound as shown in formula 3, the weight gain is 2.751% in the relative humidity range of 0% to 95%;

or, in the differential scanning calorimetry of the crystal form B of the adipate of fused ring pyrimidine compound as shown in formula 3, an absorption peak range occurs at 229° C.±5° C., and the melting heat is 144.1 J/g;

or, the differential scanning calorimetry of the crystal form B of the adipate of fused ring pyrimidine compound as shown in formula 3 is as shown in FIG. 10;

or, the crystal form B of the adipate of fused ring pyrimidine compound as shown in formula 3 is an anhydride.

12. A pharmaceutical composition, comprising a therapeutically effective amount of the crystal form B of the adipate of fused ring pyrimidine compound as shown in formula 3 as defined in claim 10.

13. A preparation method of the crystal form B of the adipate of fused ring pyrimidine compound as shown in formula 3 as defined in claim 10, comprising the following steps: reacting an alcoholic solution of adipic acid with a mixture of the fused ring pyrimidine compound as shown in formula 1 and a mixed solvent; wherein the mixed solvent is one of a mixed solvent of ketone and water, a mixed solvent of alcohol and water, and a mixed solvent of ether and water;

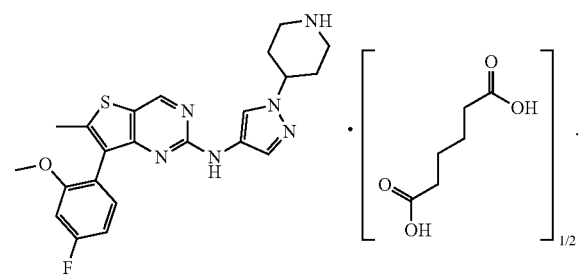

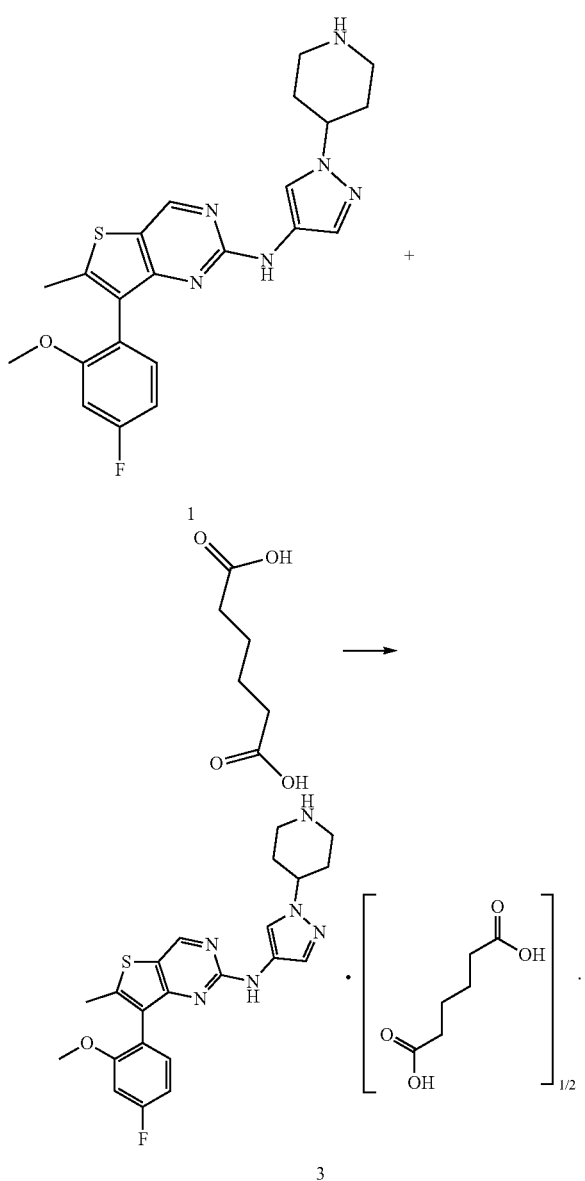

14. The preparation method as defined in claim 13, wherein the reaction is performed by dropwise adding the alcoholic solution of adipic acid into the solution of the fused ring pyrimidine compound as shown in formula 1 and the mixed solvent for reaction;

or, the mixing method of the fused ring pyrimidine compound as shown in formula 1 and the mixed solvent is to add the fused ring pyrimidine compound as shown in formula 1 into the mixed solvent;

or, the alcoholic solution of adipic acid is a methanol solution of adipic acid or an ethanol solution of adipic acid;

or, the mixed solvent is one of a mixed solvent of acetone and water, a mixed solvent of methanol or ethanol and water, and a mixed solvent of tetrahydrofuran and water;

or, the volume-to-mass ratio of the volume of the mixed solvent to the mass of the fused ring pyrimidine compound as shown in formula 1 is 40 mL/g to 110 mL/g;

or, the molar ratio of the adipic acid to the fused ring pyrimidine compound as shown in formula 1 is 0.5:1 to 3:1;

or, the temperature of the reaction is 20° C. to 60° C.;

or, the reaction time is 1 to 26 hours;

or, in the preparation method of the crystal form B of the adipate of fused ring pyrimidine compound as shown in formula 3, after the reaction is completed, the following processing steps are comprised:

cooling the reaction solution to room temperature, followed by filtration;

after the filtration, washing the resulting filter cake with the mixed solvent; and after washing the filter cake, drying the filter cake.

15. The preparation method as defined in claim 14, wherein the mixed solvent is one of a mixed solvent of acetone with 78% to 88% mass percentage concentration and water, a mixed solvent of methanol or ethanol with 90% mass percentage concentration and water, and a mixed solvent of tetrahydrofuran with 88% mass percentage concentration and water;

or, the volume-to-mass ratio of the volume of the mixed solvent to the mass of the fused ring pyrimidine compound as shown in formula 1 is 50 mL/g to 100 mL/g;

or, the molar ratio of the adipic acid to the fused ring pyrimidine compound as shown in formula 1 is 0.55:1 to 1.5:1;

or, the temperature of the reaction is 45° C. to 55° C.;

or, the cooling rate is 5° C./h;

or, the drying is vacuum drying.

16. A method for treating a tumor in a subject in need thereof, comprising administering a therapeutically effective amount of the crystal form B of the adipate of fused ring pyrimidine compound as shown in formula 3 as defined in claim 10 to the subject, wherein the tumor is selected from the group consisting of hematological tumors, colorectal cancer, gastric cancer, liver cancer and lung cancer.

* * * * *